(12) United States Patent
Kou et al.

(10) Patent No.: US 8,183,287 B2
(45) Date of Patent: May 22, 2012

(54) PHARMACEUTICAL FORMULATIONS AND COMPOSITIONS OF A SELECTIVE ANTAGONIST OF EITHER CXCR2 OR BOTH CXCR1 AND CXCR2 AND METHODS OF USING THE SAME FOR TREATING INFLAMMATORY DISORDERS

(75) Inventors: Jim H. Kou, San Jose, CA (US); Jonathan D. Eichman, Pomona, NY (US)

(73) Assignee: Schering Corporation, Kenilworth, NJ (US)

( * ) Notice: Subject to any disclaimer, the term of this patent is extended or adjusted under 35 U.S.C. 154(b) by 1365 days.

(21) Appl. No.: 11/761,588

(22) Filed: Jun. 12, 2007

(65) Prior Publication Data

US 2008/0021100 A1    Jan. 24, 2008

Related U.S. Application Data

(60) Provisional application No. 60/812,724, filed on Jun. 12, 2006.

(51) Int. Cl.
*A61K 31/27* (2006.01)
*A61K 31/135* (2006.01)
(52) U.S. Cl. ........................ 514/472; 514/648
(58) Field of Classification Search .......... 514/472, 514/648
See application file for complete search history.

(56) References Cited

U.S. PATENT DOCUMENTS

| 5,968,551 | A  | * | 10/1999 | Oshlack et al. | 424/456 |
| 7,132,445 | B2 |   | 11/2006 | Taveras et al. | |
| 2003/0143271 | A1 | * | 7/2003 | Ewing et al. | 424/468 |
| 2004/0147559 | A1 |   | 7/2004 | Taveras et al. | |
| 2008/0279822 | A1 |   | 11/2008 | Hu et al. | |

FOREIGN PATENT DOCUMENTS

| EP | 747 050 B1 | 9/2003 |
| WO | WO 02/083624 A1 | 10/2002 |
| WO | WO 03/080053 A1 | 10/2003 |
| WO | WO 2004/011418 A1 | 2/2004 |
| WO | WO 2004/094398 A2 | 11/2004 |
| WO | WO 2005/075447 A1 | 8/2005 |

OTHER PUBLICATIONS

G. Steele, Preformulation as an Aid to Product Design in Early Drug Development, Chapter 6, pp. 175-196 in Pharmaceutical Preformulation and Formulation, (M. Gibson ed. 2004).

* cited by examiner

*Primary Examiner* — Brandon Fetterolf
*Assistant Examiner* — Paul Zarek
(74) *Attorney, Agent, or Firm* — Eric A. Meade; Valerie J. Camara

(57) ABSTRACT

The present invention provides compositions as well as kits and methods based on a selective antagonist of either CXCR2 or both CXCR1 and CXCR2 that are useful for treating inflammatory disorders.

24 Claims, 8 Drawing Sheets

Part 1

Part 2

PHARMACEUTICAL FORMULATIONS AND COMPOSITIONS OF A SELECTIVE ANTAGONIST OF EITHER CXCR2 OR BOTH CXCR1 AND CXCR2 AND METHODS OF USING THE SAME FOR TREATING INFLAMMATORY DISORDERS

REFERENCE TO RELATED APPLICATION

This application claims the benefit of priority to U.S. Provisional Patent Application 60/812,724 filed Jun. 12, 2006, the entire disclosure of the priority application is hereby incorporated by reference.

FIELD OF THE INVENTION

The present invention provides compositions as well as kits and methods based on a selective antagonist of either CXCR2 or both CXCR1 and CXCR2 that are useful for treating inflammatory disorders (e.g., acute inflammatory pain, arthritis, chronic obstructive pulmonary disease (COPD), psoriasis, asthma (including neutrophilic asthma)).

BACKGROUND OF THE INVENTION

Polymorphonuclear (PMN) leukocytes, predominantly neutrophilic grunulocytes, are the most numerous white blood cells and are the first cells recruited to a site of inflammation, whereupon they release proteases, reactive oxygen species, and potent inflammatory mediators. Chemokines with the ELRCXC motif are the major mediators of neutrophil chemotaxis and share two distinct receptors, CXCR1 and CXCR2. Consequently, a selective antagonist of either or both CXCR1 and CXCR2 may prove useful in treating inflammatory disorders without the adverse side-effects associated with current therapies.

There is a need for compositions of a selective antagonist of either or both CXCR1 and CXCR2. For example, compositions that are amenable to large scale processing and have certain desirable characteristics including an immediate release dissolution profile as well as color stability.

SUMMARY OF THE INVENTION

The present invention provides compositions based on a selective antagonist of CXCR2 as well as kits and methods using the same useful for treating an inflammatory disorder. The present invention also provides compositions based on a selective antagonist of both CXCR1 and CXCR2 as well as kits and methods using the same useful for treating an inflammatory disorder. Generally, use of a selective antagonist of either CXCR2 or both CXCR1 and CXCR2 will reduce adverse side effects associated with non-selective antagonists of CXCR1 and/or CXCR2. Notably, compositions are provided that are amenable to large scale processing and have certain characteristics including a favorable dissolution profile as well as color stability.

In preferred embodiments, the selective antagonist of either CXCR2 or both CXCR1 and CXCR2 is 2-hydroxy-N,N-dimethyl-3-[[2-[[1(R)-5-methyl-2-furanyl)propyl]amino]-3,4-dioxo-1-cyclobuten-1-yl]amino]benzamide, referred to herein as Compound I, represented by the following chemical structure,

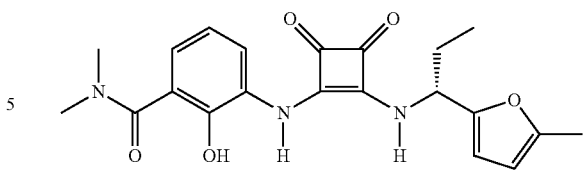

or a pharmaceutically acceptable salt thereof. In one embodiment, Compound I is a monohydrate. In one embodiment, Compound I or a pharmaceutically acceptable salt thereof is administered at a therapeutically effective amount that selectively antagonizes CXCR2. In one preferred embodiment, a therapeutically effective amount of Compound I that selectively antagonizes CXCR2 is in the range of about 3 mg per day to about 50 mg per day. In another embodiment, Compound I or a pharmaceutically acceptable salt thereof is administered at a therapeutically effective amount that selectively antagonizes both CXCR1 and CXCR2.

In preferred embodiments, the pharmaceutically acceptable salt of Compound I is prepared from a pharmaceutically acceptable acid addition salt selected from the group consisting of acetic acids benzenesulfonic acid, benzoic acid, camphorsulfonic ac d, citric acid ethanesulfonic acid, fumaric acid, gluconic acid, glutamic acid, hydrobromic acid, hydrochloric acid, isethionic acid, lactic acid, maleic acid, malic acid, mandelic acid, methanesulfonic acids mucic acid, nitric acid, pamoic acid, pantothenic acid, phosphoric acid, succinic acid, sulfuric acid, tartaric acid, and p-toluene sulfonic acid.

The present invention provides a composition comprising a selective antagonist of CXCR2 and at least one pharmaceutically acceptable excipient. The present invention also provides a composition comprising a selective antagonist of both CXCR1 and CXCR2 and at least one pharmaceutically acceptable excipient. In a preferred embodiment, the selective antagonist of both CXCR1 and CXCR2 is Compound I or a pharmaceutically acceptable salt thereof.

The present invention provides a composition comprising Compound I or a pharmaceutically acceptable salt thereof and at least one pharmaceutically acceptable excipient which provides release of at least about 83% Compound I in 5 minutes when tested using a USPII Paddle Stirrer apparatus filled with 900 mL of dissolution medium consisting of 0.5% sodium lauryl sulfate solution buffered with pH 6.8 sodium phosphate buffer at 37° C.±0.5° C. with the paddle speed set at 75 RPM. Preferably, the composition provides release of at least about 99% Compound I in 15 minutes.

In one embodiment, at least one pharmaceutically acceptable excipient is one or more wetting agent(s), one or more binder(s), one or more diluent(s), or one or more disintegrant(s). In an another embodiment, at least one pharmaceutically acceptable excipient is one or more wetting agent(s), one or more binder(s), one or more diluent(s), and one or more disintegrant(s) In yet another embodiment, at least one pharmaceutically acceptable excipient is a wetting agent, a binder, a diluent, or a disintegrant, or any combination of two or more thereof.

In one embodiment, the composition is color stable as assessed by comparing the color of a first sample taken after blending Compound I, one or more wetting agent(s), one or more binder(s), one or more diluent(s), and one or more disintegrant(s) in a fluid bed with a second sample taken after loss on drying ≦4% reached under an inlet air temperature of 70° C. and the second sample is continued to dry under the inlet air temperature of 70° C. for at least 80 minutes.

In one embodiment of the composition, one or more wetting agent(s) is present at about 0.1-8% (w/w). In one embodiment, one or more wetting agent(s) is sodium laurel sulfate present in a ratio of sodium laurel sulfate to Compound I of about 1 to 10. In one embodiment, one or more wetting agent(s) is sodium laurel sulfate present in a range of about 0.1% to about 5% (w/w). Preferably, one or more wetting agent(s) is sodium laurel sulfate present in a range of about 0.1% to about 2% (w/w), more preferably at about 1.5% (w/w).

The present invention also provides a composition comprising Compound I or a pharmaceutically acceptable salt thereof and at least one pharmaceutically acceptable excipient, which provides release of at least about 92% Compound I in 15 minutes when tested using a USPII Paddle Stirrer filled with 900 mL of dissolution medium consisting of 0.2% SLS solution buffered with pH 7.4 sodium phosphate buffer at 37° C.±0.5° C. with the paddle speed set at 75 RPM. Preferably, the composition provides release of at least about 96% Compound I in 30 minutes.

In one embodiment, at least one pharmaceutically acceptable excipient is one or more wetting agent(s), one or more binder(s), one or more diluent(s), or one or more disintegrant(s). In an another embodiment, at least one pharmaceutically acceptable excipient is one or more wetting agent(s), one or more binder(s), one or more diluent(s), and one or more disintegrant(s). In yet another embodiment, at least one pharmaceutically acceptable excipient is a wetting agent, a binder, a diluent, or a disintegrant, or any combination of two or more thereof.

In one embodiment of the composition, one or more wetting agent(s), one or more binder(s), one or more diluent(s), and one or more disintegrant(s) are blended in a fluid bed. In one embodiment, one or more wetting agent(s) is poloxamer present in a ratio of poloxamer to Compound I of between about 0.3:1 to about 1.2:1. Preferably, the ratio of poloxamer to Compound I is about 1.2 to 1. In one embodiment, one or more wetting agent(s) is poloxamer present at about 0.1-8% (w/w).

In one embodiment, one or more binder(s) is present at about 0.1% to about 20% (w/w). In one preferred embodiment, one or more binder(s) is povidone present in a ratio of povidone to Compound I of between about 0.18:1 to about 1.8:1. In another preferred embodiment, the ratio of povidone to Compound I is about 0.66 to 1. In one embodiment, one or more binder(s) is povidone present at about 0.3% to about 5% (w/w). In one embodiment, one or more binder(s) is povidone present at about 2% to about 3% (w/w).

In one embodiment, the composition is stable for at least 6 months at 40° C./75% relative humidity (RH) when packaged in high density polyethylene bottles (HDPE) bottles. Preferably, the composition is stable for at least 18 months at 25° C./60% RH when packaged in high density polyethylene bottles (HOPE) bottles.

In one embodiment, one or more binder(s) is pregelatinized starch present at about 0.1% to about 20% (w/w). In one preferred embodiment, pregelatinized starch is present at a ratio of pregelatinized starch to Compound I of between about 0.3:1 to about 1.2:1. In another preferred embodiment, pregelatinized starch is present at about 6% to about 7% (w/w).

In one embodiment, one or more diluent(s) is present at about 10% to about 90% (w/w). In one preferred embodiment, one or more diluent(s) is microcrystalline cellulose and lactose.

In one embodiment, one or more disintegrant(s) is present at about 2% to about 30% (w/w). In one preferred embodiment, one or more disintegrant(s) is crospovidone.

In one embodiment, the composition further comprises one or more glidant(s). In one preferred embodiment, one or more glidant(s) is present at about 0.1% to about 5% (w/w). In one preferred embodiment, one or more glidant(s) is silicon dioxide.

In one embodiment, the composition further comprises one or more lubricant(s). Preferably, one or more lubricant(s) is present at about 0.2% to about 5% (w/w). In one preferred embodiment, one or more lubricant(s) is magnesium stearate.

The present invention also provides a composition comprising the following components:

| Components | mg per unit dose of composition |
|---|---|
| Compound I | 3 |
| Lactose Monohydrate | 115.72 |
| Microcrystalline Cellulose | 35.2 |
| Crospovidone | 16.5 |
| Povidone | 5.28 |
| Sodium Lauryl Sulfate | 0.3 |

In one embodiment, the composition further comprises the following components:

| Components | mg per unit dose of composition |
|---|---|
| Microcrystalline Cellulose | 24.2 |
| Crospovidone | 16.5 |

In one embodiment, the composition further comprises the following components:

| Components | mg per unit dose of composition |
|---|---|
| Silicon Dioxide | 2.2 |
| Magnesium Stearate | 1.1 |

The present invention also provides a composition comprising the following components:

| Components | mg per unit dose of composition |
|---|---|
| Compound I | 10 |
| Lactose Monohydrate | 108.02 |
| Microcrystalline Cellulose | 35.2 |
| Crospovidone | 16.5 |
| Povidone | 5.28 |
| Sodium Lauryl Sulfate | 1 |

In one embodiment, the composition further comprises the following components:

| Components | mg per unit dose of composition |
|---|---|
| Microcrystalline Cellulose | 24.2 |
| Crospovidone | 16.5 |

In one embodiment, the composition further comprises the following components:

| Components | mg per unit dose of composition |
| --- | --- |
| Silicon Dioxide | 2.2 |
| Magnesium Stearate | 1.1 |

The present invention also provides a composition comprising the following components:

| Components | mg per unit dose of composition |
| --- | --- |
| Compound I | 30 |
| Lactose Monohydrate | 86.02 |
| Microcrystalline Cellulose | 35.2 |
| Crospovidone | 16.5 |
| Povidone | 5.28 |
| Sodium Lauryl Sulfate | 3 |

In one embodiment, the composition further comprises the following components:

| Components | mg per unit dose of composition |
| --- | --- |
| Microcrystalline Cellulose | 24.2 |
| Crospovidone | 16.5 |

In one embodiment, the composition further comprises the following components:

| Components | mg per unit dose of composition |
| --- | --- |
| Silicon Dioxide | 2.2 |
| Magnesium Stearate | 1.1 |

The present invention also provides a composition comprising the following components:

| Components | Mg per unit dose of composition |
| --- | --- |
| Compound I | 1 |
| Lactose Monohydrate | 5.64 |
| Microcrystalline Cellulose | 2.8 |
| Crospovidone | 2.8 |
| Poloxamer 188 | 1.2 |
| Povidone | 0.66 |
| Silicon Dioxide | 0.1 |

In one embodiment, the composition further comprises the following components;

| Components | Mg per unit dose of composition |
| --- | --- |
| Lactose Monohydrate | 50.6 |
| Microcrystalline Cellulose | 120 |
| Crospovidone | 12.2 |

In one embodiment, the composition further comprises the following components:

| Components | Mg per unit dose of composition |
| --- | --- |
| Silicon Dioxide | 2 |
| Magnesium Stearate | 1 |

The present invention also provides a composition comprising the following components:

| Components | Mg per unit dose of composition |
| --- | --- |
| Compound I | 10 |
| Lactose Monohydrate | 56.4 |
| Microcrystalline Cellulose | 28 |
| Crospovidone | 28 |
| Poloxamer 188 | 12 |
| Povidone | 6.6 |
| Silicon Dioxide | 1 |

In one embodiment, the composition further comprises the following components:

| Components | Mg per unit dose of composition |
| --- | --- |
| Lactose Monohydrate | 58 |
| Microcrystalline Cellulose | 8 |
| Crospovidone | 10 |

In one embodiment, the composition further comprises the following components:

| Components | Mg per unit dose of composition |
| --- | --- |
| Silicon Dioxide | 1 |
| Magnesium Stearate | 1 |

The present invention also provides a composition comprising the following components:

| Components | Mg per unit dose of composition |
| --- | --- |
| Compound I | 10 |
| Lactose Monohydrate | 57.5 |
| Microcrystalline Cellulose | 28.8 |
| Crospovidone | 28 |
| Starch Pregelatinized | 12 |
| Poloxamer 188 | 12 |

In one embodiment, the composition further comprises the following components:

| Components | Mg per unit dose of composition |
|---|---|
| Microcrystalline Cellulose | 28.8 |
| Crospovidone | 8 |
| Starch Pregelatinized | 12 |

In one embodiment, the composition further comprises the following components:

| Components | Mg per unit dose of composition |
|---|---|
| Silicon Dioxide | 2 |
| Magnesium Stearate | 1 |

The present invention also provides a composition comprising the following components:

| Components | Mg per unit dose composition |
|---|---|
| Compound I | 50 |
| Lactose Monohydrate | 55.3 |
| Microcrystalline Cellulose | 25.1 |
| Crospovidone | 32.5 |
| Starch Pregelatinized | 15 |
| Poloxamer 188 | 15 |

In one embodiment, the composition further comprises the following components:

| Components | Mg per unit dose of composition |
|---|---|
| Microcrystalline Cellulose | 25.1 |
| Crospovidone | 12.5 |
| Starch Pregelatinized | 15 |

In one embodiment, the composition further comprises the following components:

| Components | Mg per unit dose of composition |
|---|---|
| Silicon Dioxide | 3 |
| Magnesium Stearate | 1.5 |

In one embodiment, the composition exhibits a mean AUC of Compound I between about 484 ng.hr/ml and about 489 ng.hr/ml following a single-dose oral administration of 30 mg Compound I to a human. In one embodiment, the composition exhibits mean Cmax of Compound I between about 122 ng/ml and about 147 ng/ml following a single-dose oral administration of 30 mg Compound I to a human. In one embodiment, the composition exhibits a median Tmax of Compound I between about 0.5 and about 2 hours following oral administration to a human.

In a preferred embodiment, the present invention provides kits comprising.
a container having a therapeutically effective amount of a selective antagonist of either CXCR2 or both CXCR1 and CXCR2;
instructions for use to treat an inflammatory disorder.

In one embodiment of the kit, the selective antagonist of both CXCR1 and CXCR2 is Compound I or a pharmaceutically acceptable salt thereof. In another embodiment of the kit, Compound I or a pharmaceutically acceptable salt thereof is present in a unit dosage form containing about 3 mg, about 10 mg, or about 30 mg of Compound I or a pharmaceutically acceptable salt thereof.

The present invention also provides methods for treating an inflammatory disorder in a patient suffering therefrom comprising administering a therapeutically effective amount of the compositions described herein. In preferred embodiments, the inflammatory disorder is selected from acute inflammatory pain, arthritis, COPD, psoriasis, and asthma. In one preferred embodiment, the inflammatory disorder is COPD. In another preferred embodiment, the inflammatory disorder is psoriasis. In yet another preferred embodiment, the inflammatory disorder is asthma. In still yet another preferred embodiment, the inflammatory disorder is neutrophilic asthma.

In one embodiment, the therapeutically effective amount of Compound I or a pharmaceutically acceptable salt thereof is about 3 mg to about 200 mg per day. In another embodiment, the therapeutically effective amount of Compound I or a pharmaceutically acceptable salt thereof is about 3 mg to about 50 mg of Compound I or a pharmaceutically acceptable salt thereof per day. In yet another embodiment, the therapeutically effective amount of Compound I or a pharmaceutically acceptable salt thereof is orally administered in a unit dosage form containing about 3 mg, about 10 mg, or about 30 mg of Compound I or a pharmaceutically acceptable salt thereof.

BRIEF DESCRIPTION OF THE DRAWINGS

FIG. 2 illustrates the mean plasma concentration of Compound I (in the form of capsules containing Formulation 1) following a single oral dose of 10, 50, 100, 150 (alone or coadministered with filgrastim (human G-CSF)) or 200 mg of Compound I to healthy subjects. In particular.

FIG. 4 illustrates a schematic of a clinical study designed to demonstrate the effect of Compound I in subjects with moderate to severe COPD. In particular.

FIG. 5 illustrates a schematic of a clinical study designed to demonstrate the effect of Compound I in subjects with severe neutrophilic asthma. In particular.

FIG. 6 illustrates a schematic of a clinical study designed to demonstrate the effect of Compound I in subjects with severe psoriasis. In particular, In particular.

DETAILED DESCRIPTION OF THE INVENTION

Figure 1:
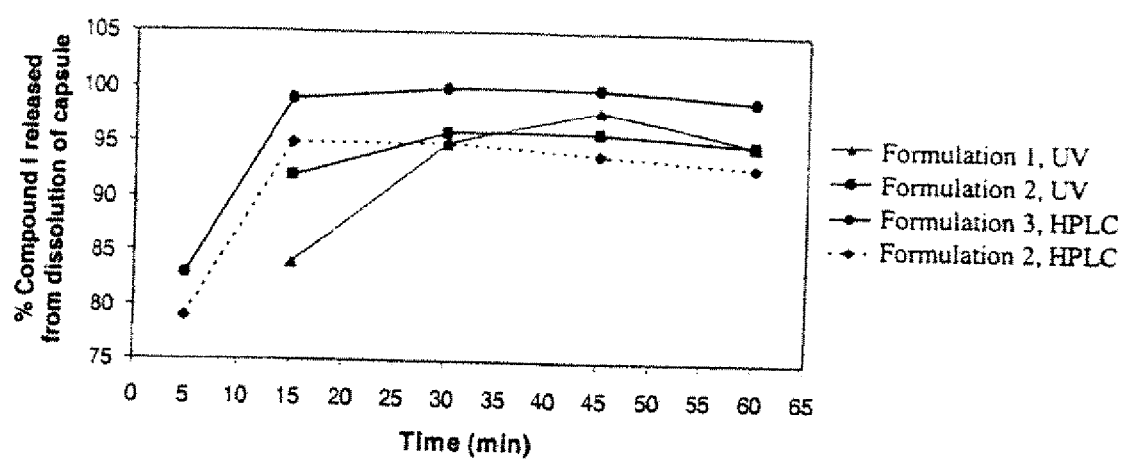
FIG. 1 illustrates the percent Compound I released from the dissolution of granule Formulations 1, 2, and 3 placed into capsules vs. time. See Example 3, infra, for details.

As used herein, the following terms shall have the definitions set forth below.

As used herein, the phrase "selective antagonist of CXCR2" means an agent that inhibits CXCR2, signaling with more than about 10-fold greater potency than from one or more other chemokines. Similarly, the phrase "selective antagonist of both CXCR1 and CXCR2" means an agent that inhibits CXCR1 and CXCR2 signaling with more than about 10-fold greater potency than from one or more other chemokines.

Compound I is a highly selective, potent, non-competitive, reversible dual antagonist of human CXCR1 (Kd=4 nM) and human CXCR2 (Kd=0.05 nM) based on extensive in vitro analyses using cloned receptors, neutrophil membranes and intact neutrophils. Orally administered Compound I effectively blocks neutrophil recruitment to the lungs of monkeys, rats and mice and to the pleural cavities of rats and mice in response to diverse challenges including LPS, vanadium pentoxide, antigen and mechanical irritation. Compound I compares very favorably with NSAIDs in its ability to inhibit carrageenan-induced paw edema in rats. Prolonged treatment with Compound I blocks pulmonary mucin production in rats and mice as well as histological changes in arthritic joints of rats. This activity profile of Compound I indicates its utility as a novel, effective treatment for inflammatory disorders. WO 02/083624 describes this compound (as Examples 360.31 and 405), process of making the same, as well as treatment of chemokine-related diseases and cancer using the same. Likewise, WO 03/080053 describes the treatment of chemokine-related diseases using this compound. WO 20041094398 describes a novel process for preparing this compound and WO 2005/075447 describes polymorphic forms I-IV of this compound as well processes for preparing the same. In one embodiment, polymorph form III is preferred. In another embodiment, polymorph form IV is preferred.

As used herein, the phrase "therapeutically effective amount" with respect to a selective antagonist of either CXCR2 or both CXCR1 and CXCR2 means an amount which provides a therapeutic benefit in the treatment or management of the referenced inflammatory disorder (e.g., acute inflammatory pain, arthritis, COPD, psoriasis, asthma (including neutrophilic asthma)).

As used herein the phrase "pharmaceutically acceptable salt" refers to a non-toxic salt prepared from a pharmaceutically acceptable acid or base (including inorganic acids or bases, or organic acids or bases). Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylgulcaine), lysine, and procaine. As used herein, the phrase "inflammatory disorder" refers to an inflammatory disorder that involves signaling via CXCR1 and/or CXCR2. In more preferred embodiments, the compositions, kits, and methods of the invention are used to treat acute inflammatory pain, arthritis, COPD, psoriasis, and asthma (including neutrophilic asthma).

As used herein, the term "treating" is intended to mean mitigating or alleviating an inflammatory disorder (e.g., acute inflammatory pain, arthritis, COPD, psoriasis, asthma (including neutrophilic asthma)) in a mammal such as a human.

As used herein the term "capsule" refers to a special container or enclosure made of methyl cellulose, polyvinyl alcohols, or denatured gelatins or starch for holding or containing a composition comprising a composition of the present invention and a carrier. There are soft shell gel capsules and hard shell gel capsules, In contrast to soft shell gel capsules, hard shell gel capsules are typically made of blends of relatively high gel strength bone and pork skin gelatins. The capsule itself may contain small amounts of dyes, opaquing agents, plasticizers, and preservatives.

As used herein the term "tablet" refers to an orally disintegrating tablet containing a composition comprising a composition of the present invention and a carrier with suitable diluents. The tablet can be prepared by soft compression of mixtures or granulations or by lyophilization.

As used herein the phrase "oral gel" refers to a composition comprising a composition of the present invention and a carrier dispersed or solubilized in a hydrophilic semi-solid matrix.

As used herein the phrase "orally consumable film" refers to a composition comprising a composition of the present invention and an edible film carrier.

As used herein the phrase "powders for constitution" refers to powder blends containing a composition comprising a composition of the present invention and a carrier with suitable diluents which can be suspended in water or juices.

As used herein the term "diluent" refers to a substance that usually makes up the major portion of the composition. Suitable diluents include sugars such as lactose, sucrose, mannitol, and sorbitol; starches derived from wheat, corn rice, and potato; and celluloses such as microcrystalline cellulose. The amount of diluent in the composition can range from about 10% to about 90% by weight of the total composition, preferably from about 25% to about 90% by weight, more preferably from about 25% to about 80%, more preferably from about 30% to about 80% by weight, even more preferably from about 65% to about 80% by weight.

As used herein the term "disintegrant" refers to a substance added to the composition to help it break apart (disintegrate) and release the medicinal agent(s). Suitable disintegrants include starches; "cold water soluble" modified starches such as sodium carboxymethyl starch; natural and synthetic gums such as locust bean, karaya, guar, tragacanth, and agar; cellulose derivatives such as methylcellulose and sodium carboxymethylcellulose, microcrystalline celluloses and cross-linked microcrystalline celluloses such as sodium croscarmellose; alginates such as alginic acid and sodium alginate; clays such as bentonites; effervescent mixtures; and super-disintegrants such as sodium starch glycolate, crospovidone, and croscarmellose sodium. The amount of disintegrant in the composition can range from about 2% to about 30% by weight of the composition, preferably from about 4% to about 22% by weight, more preferably from about 4% to about 17% by weight, even more preferably from about 4% to about 15% by weight.

As used herein the term "binder" refers to a substance that binds or "glues" powders together and makes them cohesive by forming granules, thus serving as the "adhesive" in the composition. Binders add cohesive strength already available in the diluent or bulking agent. Suitable binders include sugars such as sucrose; starches derived from wheat, corn rice, and potato, including pregelatinized starch; natural gums such as acacia, gelatin, and tragacanth; derivatives of seaweed such as alginic acid, sodium alginate, and ammonium calcium alginate; cellulosic materials such as methylcellulose, sodium carboxymethylcellulose, and hydroxypropylmethylcellulose; polyvinylpyrrolidinone; and inorganics such as magnesium aluminum silicate. The amount of binder in the composition can range from about 0.1% to about 20% by weight of the composition, preferably from about 0.3% to about 10% by weight, more preferably 0.3% to about 5% by weight, even more preferably from about 0.3% to about 3% by weight.

As used herein the term "lubricant" refers to a substance added to the composition to enable the granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols, and d'l-leucine. Lubricants are usually added at the very last step before compression, since they must be present on the surfaces of the granules and in between them and the parts of the tablet press. The amount of lubricant in the composition can range from about 0.2% to about 5% by weight of the composition, preferably from about 0.5% to about 2%, more preferably from about 0.3% to about 1.5% by weight.

As used herein the term "glidant" refers to a substance that prevents caking and improves the flow characteristics of granulations, so that flow is smooth and uniform. Suitable glidants include silicon dioxide and talc. The amount of glidant in the composition can range from about 0.1% to about 5% by weight of the total composition, preferably from about 0.5% to about 2% by weight.

As used herein the phrase "wetting agent" refers to a substance that allows the composition to be wetted by lowering its surface tension. Wetting agents may be anionic, cationic, or nonionic. Suitable wetting agents include docusate sodium, emulsifying wax BP, self-emulsifying glyceryl monooleate, sodium lauryl sulfate, benzethonium chloride, cetrimide, sodium lauryl sulfate incompatibility, chlorhexidine activity, emulsifying waxes, butylparaben, emulsifying wax USP, ethylparaben, glyceryl monooleate, methylparaben, polyoxyethylene alkyl ethers, polyoxyethylene castor oil derivatives, polyoxyethylene sorbitan fatty acid esters, polyoxyethylene stearates, polysorbate 80, propylparaben, sorbic acid, sorbitan esters, and triethyl citrate. The amount of the wetting agent can vary from about 0.1% to about 8% by weight of the composition, more preferably, 0.1% to about 5% by weight of the composition, yet more preferably from about 0.1% to about 1%.

In one embodiment, the compositions and kits of the present invention are for oral administration. For oral preparations, a pharmaceutically acceptable carrier (which includes diluents, excipients, or carrier materials) is also present in the composition. The carrier is suitably selected with respect to the intended form of administration, i.e., oral capsules (either solid-filled, semi-solid (gel) filled, or liquid filled), powders for constitution, oral gels, orally disintegrating tablet, orally consumable films, elixirs, syrups, suspensions, and the like, and consistent with conventional pharmaceutical practices. For example, for oral administration in the form of capsules, the pharmaceutically active agents may be combined with any oral non-toxic pharmaceutically acceptable inert carrier, such as lactose, starch, sucrose, cellulose, magnesium stearate, dicalcium phosphate, calcium sulfate, mannitol, ethyl alcohol (liquid forms), and the like. Moreover, when desired or needed, suitable binders, lubricants, disintegrants, disinfectants and coloring agents may also be incorporated in the mixture. Suitable binders include starch, gelatin, natural sugars, corn sweeteners, natural and synthetic gums such as acacia, sodium alginate, carboxymethylcellulose, polyethylene glycol, and waxes. Suitable lubricants include boric acid, sodium benzoate, sodium acetate, sodium chloride, and the like. Suitable disintegrants include starch, methylcellulose, guar gum, and the like. Suitable disinfectants include benzalkonium chloride and the like. Sweetening and flavoring agents and preservatives may also be included where appropriate.

Additionally, the compositions and kits of the present invention may be formulated in sustained release form to provide the rate controlled release of any one or more of the pharmaceutically active agents to optimize the therapeutic effects. Suitable compositions for sustained release include layered capsules (e.g., containing layers of varying disintegration rates or controlled release polymeric matrices impregnated with the medicinal agents) that are shaped in capsules containing such impregnated or encapsulated porous polymeric matrices.

In another embodiment, the compositions and kits of the present invention are for parenteral administration, for example, intravenous, intratumoral, subcutaneous, or intramuscular administration.

Thus, to prepare an aqueous solution for parenteral injection, it is possible to use a co-solvent, e.g., an alcohol such as ethanol or a glycol such as polyethylene glycol or propylene glycol, or glycerin, and optionally, a hydrophilic surfactant such as Tween® 80. An oily solution injectable intramuscularly can be prepared, e.g., by solubilizing the active principle with a triglyceride or a glycerol ester. The substantially non-aqueous carrier (excipient) can be any substance that is biocompatible and liquid or soft enough at body temperature. The carrier is usually hydrophobic and commonly organic, e.g., an oil or fat of vegetable, animal, mineral or synthetic origin or derivation. Preferably, but not necessarily, the carrier includes at least one chemical moiety of the kind that typifies "fatty" compounds, e.g., fatty acids, alcohols, esters, etc., i.e., a hydrocarbon chain, an ester linkage, or both. "Fatty" acids in this context include acetic, propionic and butyric acids, through straight- or branched-chain organic acids containing up to 30 or more carbon atoms.

Preferably, the carrier is immiscible in water and/or soluble in the substances commonly known as fat solvents. The carrier can correspond to a reaction product of such a "fatty" compound or compounds with a hydroxy compound, e.g., a mono-hydric, di-hydric, trihydric or other polyhydric alcohol, e.g., glycerol, propanediol, lauryl alcohol, polyethylene or -propylene glycol, etc. These compounds include the fat-soluble vitamins, e.g., tocopherols and their esters, e.g., acetates sometimes produced to stabilize tocopherols. Sometimes, for economic reasons, the carrier may preferably comprise a natural, unmodified vegetable oil such as sesame oil, soybean oil, peanut oil, palm oil, or an unmodified fat. Alternatively the vegetable oil or fat may be modified by hydrogenation or other chemical means which is compatible with the present invention. The appropriate use of hydrophobic substances prepared by synthetic means is also envisioned.

Pharmaceutical compositions suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g., human serum albumin), toxicity agents (e.g., NaCl), preservatives (e.g., thimerosol, cresol or benylalcohol), and surfactants (e.g., Tween or polysorabates) in sterile water for injection.

Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized powder in a separate compartment.

Generally, an amount of selective antagonist of either or both CXCR1 and CXCR2 to be administered is decided on a case by case basis by the attending physician. As a guideline, the extent of the inflammatory disorder, the body weight, and the age of the patient will be considered, among other factors, when seeing an appropriate dose.

Exemplary compositions of Compound I are detailed below in Tables 1-4. Formulation 1 capsules containing Compound I is detailed in Table 1.

TABLE 1

| Components | Amount per capsule (mg) | |
| --- | --- | --- |
| | 10 mg Compound I capsule | 50 mg Compound I capsule |
| Compound I | 10 | 50 |
| Lactose Monohydrate | 57.5 | 55.3 |
| Microcrystalline Cellulose | 28.8 | 25.1 |
| Crospovidone | 28 | 32.5 |
| Starch Pregelatinized | 12 | 15 |
| Poloxamer 188 | 12 | 15 |
| Purified Water USP | —[a] | —[a] |
| Total Granule Weight | 124.3 | 162.9 |
| Capsule Fill | | |
| Monohydrate Granules | 124.3 | 162.9 |
| Microcrystalline Cellulose | 28.8 | 25.1 |
| Crospovidone | 8 | 12.5 |
| Starch Pregelatinized | 12 | 15 |
| Silicon Dioxide | 2 | 3 |
| Magnesium Stearate | 1 | 1.5 |
| Capsule Fill Weight | 176 | 220 |
| Capsule Shell | | |
| Hard Gelatin Capsule, No. 2 Blue Opaque[b] | 60 | — |
| Hard Gelatin Capsule, No. 1 Blue Opaque[c] | — | 75 |
| | 0 | 0 |
| Total Filled Capsule Weight | 236 | 295 |

[a]Evaporates during the manufacturing process
[b]Contains 0.8867% FD&C Blue #2, 1.4393% Titanium Dioxide, and qs 100% gelatin.
[c]Contains 0.8867% FD&C Blue #1, 1.4393% Titanium Dioxide, and qs 100% gelatin.

Formulation 1 capsules were manufactured via wet granulation using a low shear mixing process, drying, milling, blending, and encapsulation in hard gelatin capsules. These capsules were found to be stable for at least 6 months at 40° C./75% relative humidity (RH), and for at least 18 months at 25° C./60% RH when packaged in high density polyethylene bottles (HDPE) bottles.

Formulation 1, however, was not amenable to large scale processing due to the low-shear mixing process which is impractical for large scale processing. To facilitate a process scale-up using the wet granulation method, the low shear mixing process was replaced by a fluidized bed process. This change in manufacture however, also required a modification in the formulation as pregelatinized starch, the binder used in Formulation 1, is incompatible with the fluidized bed process adopted. Therefore, another binder compatible with both the fluidized bed process and Compound I was required. Povidone was subsequently identified as a suitable binder and employed in place of pregelatinized starch at an entirely different concentration. Formulation 2 containing Compound I as well as povidone is detailed in Table 2.

TABLE 2

| Components | Amount per capsule (mg) | |
| --- | --- | --- |
| | 1 mg Compound I capsule | 10 mg Compound I capsule |
| Monohydrate Granules | | |
| Compound I | 1 | 10 |
| Lactose Monohydrate | 5.64 | 56.4 |
| Microcrystalline Cellulose | 2.8 | 28 |
| Crospovidone | 2.8 | 28 |
| Poloxamer 188 | 1.2 | 12 |
| Povidone | 0.66 | 6.6 |
| Silicon Dioxide | 0.1 | 1 |
| Purified Water USP | —[a] | —[a] |
| Total Granule Weight | 14.2 | 142 |
| Capsule Fill | | |
| Monohydrate Granules | 14.2 | 142 |
| Lactose Monohydrate | 50.6 | 58 |
| Microcrystalline Cellulose | 120 | 8 |
| Crospovidone | 12.2 | 10 |
| Silicon Dioxide | 2 | 1 |
| Magnesium Stearate | 1 | 1 |
| Capsule Fill Weight | 200 | 220 |
| Capsule Shell | | |
| Hard Gelatin Capsule, No. 2 Blue Opaque[b] | 60 | 60 |
| | 0 | 0 |
| Total Filled Capsule Weight | 260 | 280 |

[a]Evaporates during the manufacturing process
[b]Contains 0.8867% FD&C Blue #2, 1.4393% Titanium Dioxide, and qs 100% gelatin.

Formulation 2 capsules were manufactured via wet granulation using a fluidized bed, drying, milling, blending, and encapsulation in hard gelatin capsules. Although amenable to large scale processing, Formulation 2 capsules were found to discolor during manufacture.

To provide formulations that are both amenable to large scale processing by wet granulation and that result in a more color stable product, the color stability of individual excipients in combination with Compound I were explored as detailed in Example 1 below. Based on the results from these analyses, other formulations were developed that employed a different concentration of the wetting agent poloxamer (i.e., 3% or 8%) or an entirely different wetting agent, sodium lauryl sulfate (SLS) at an entirely different concentration (i.e., 1.5%). Exemplary formulations using poloxamer or SLS are provided in Table 3.

TABLE 3

| Components | Amount per capsule (mg) | |
| --- | --- | --- |
| | Formulation A | Formulation B |
| Compound I (polymorph Form III), micronized | 30 | 30 |
| Lactose Monohydrate NF | 80.9 | 129 |
| Cellulose Microcrystalline NF (Avicel PH 102) | 13.4 | 20 |
| Crospovidone NF | 15.7 | 10 |
| Povidone K29/32 | 7.4 | 8 |
| Poloxamer 188 NF | 12.8 | — |
| SLS | — | 3 |
| Total | 160 | 200 mg |

The color stability of formulations using poloxamer or SLS were explored as detailed in Example 2 below. Based on the increased color stability of Exemplary Formulation B which employs SLS as a wetting agent at 1.5% instead of poloxamer at either 3% or 8%, Formulation 3 containing Compound I and SLS was developed, Formulation 3 is detailed in Table 4,

TABLE 4

| | Amount per capsule (mg) | | |
| --- | --- | --- | --- |
| Components | 3 mg Compound I capsule | 10 mg Compound I capsule | 30 mg Compound I capsule |
| Monohydrate Granules | | | |
| Compound I | 3 | 10 | 30 |
| Lactose Monohydrate | 115.72 | 108.02 | 86.02 |
| Microcrystalline Cellulose | 35.2 | 35.2 | 35.2 |
| Crospovidone | 16.5 | 16.5 | 16.5 |
| Povidone | 5.28 | 5.28 | 5.28 |
| Sodium Lauryl Sulfate | 0.3 | 1 | 3 |
| Purified Water USP | —[a] | —[a] | —[a] |
| Total Granule Weight | 176 | 176 | 176 |
| | Capsule Fill | | |
| Monohydrate Granules | 176 | 176 | 176 |
| Microcrystalline Cellulose | 24.2 | 24.2 | 24.2 |
| Crospovidone | 16.5 | 16.5 | 16.5 |
| Silicon Dioxide | 2.2 | 2.2 | 2.2 |
| Magnesium Stearate | 1.1 | 1.1 | 1.1 |
| Capsule Fill Weight | 220 | 220 | 220 |
| | Capsule Shell | | |
| Hard Gelatin Capsule, No. 2 Blue Opaque[b] | 60 0 | 60 0 | 60 0 |
| Total Filled Capsule Weight | 280 | 280 | 280 |

[a]Evaporates during the manufacturing process
[b]Contains 0.8867% FD&C Blue #2, 1.4393% Titanium Dioxide, and qs 100% gelatin.

Formulation 3 capsules were manufactured in a manner similar to Formulation 2 via wet granulation using a fluidized bed, drying, milling, blending, and encapsulation.

EXAMPLES

Example 1

Study to Evaluate the Color Stability of Individual Excipients with Compound I

The color stability of individual excipients in combination with Compound I were explored in the following three experiments detailed below.

Experiment A—60° C. Incubation

Vials without caps containing either Compound I with an excipient (mixed well) or excipient alone were placed in a 60° C. oven for 6 hours. The weight of each component in the vials examined is detailed in Table 5.

TABLE 5

| Sample | Compound I (mg) | SLS (mg) | Poloxamer (mg) | Lactose (mg) | Avicel (mg) | PVP (mg) | Crospovidone (mg) |
| --- | --- | --- | --- | --- | --- | --- | --- |
| A1 | 90.3 | 91.3 | | | | | |
| A2 | 91.2 | | 90.3 | | | | |
| A3 | 90.7 | | | 91.3 | | | |
| A4 | 91.4 | | | | 90.4 | | |
| A5 | 90.2 | | | | | 90.8 | |
| A6 | 91.1 | | | | | | 91.0 |
| A7 | 90.9 | | | | | | |
| A8 | | 92.0 | | | | | |
| A9 | | | 91.4 | | | | |
| A10 | | | | 90.3 | | | |
| A11 | | | | | 90.4 | | |
| A12 | | | | | | | |
| A13 | | | | | | | 90.7 |

After 6 hours at 60° C., the vials were removed, caps placed on the vials, and a visual observation recorded. The visual observation for each sample is summarized below in Table 6.

TABLE 6

| Sample | Visual observation |
|---|---|
| A1 | White to slight off white powder |
| A2 | Off white liquid then solidified at room temperature (RT) |
| A3 | White to off white powder |
| A4 | White powder |
| A5 | White powder |
| A6 | White to slight off white |
| A7 | White to slight off white |
| A8 | White powder |
| A9 | Clear liquid, solidified at RT. |
| A10 | White powder |
| A11 | Off white to white powder |
| A12 | White powder |
| A13 | White/off white powder |

Experiment B—70° C. Incubation

Vials without caps containing either Compound I with an excipient (mixed well) or excipient alone were placed in a 70° C. oven for 6 hours. The weight of each component in the vials examined is detailed in Table 7.

TABLE 7

| Sample | Compound I (mg) | SLS (mg) | Poloxamer (mg) | Lactose (mg) | Avicel (mg) | PVP (mg) | Crospovidone (mg) |
|---|---|---|---|---|---|---|---|
| A1 | 90.4 | 91.3 | | | | | |
| A2 | 91.2 | | 91.1 | | | | |
| A3 | 90.6 | | | 91.4 | | | |
| A4 | 90.7 | | | | 92.5 | | |
| A5 | 91.0 | | | | | 91.2 | |
| A6 | 90.9 | | | | | | 90.4 |
| A7 | 91.1 | | | | | | |
| A8 | | 91.3 | | | | | |
| A9 | | | 90.2 | | | | |
| A10 | | | | 92.1 | | | |
| A11 | | | | | 90.4 | | |
| A12 | | | | | | 91.3 | |
| A13 | | | | | | | 92.5 |

After 6 hours at 70° C., the vials were removed, caps placed on the vials, and a visual observation recorded. The visual observation for each sample is summarized below in Table 8.

TABLE 8

| Sample | Visual observation |
|---|---|
| B1 | White powder to slight off white |
| B2 | Yellow liquid when first taken out of oven. Solidified at RT (turned off white to slight yellow) |
| B3 | White powder |
| B4 | White powder |
| B5 | White powder |
| B6 | White powder to slight off white |
| B7 | White powder |
| B8 | White powder |
| B9 | Clear liquid - solidified at RT |
| B10 | White powder |
| B11 | White powder to slight off white |
| B12 | White powder |
| B13 | White powder to slight off white |

Experiment C—70° C. Incubation (with Water)

Vials with caps containing either Compound I with an excipient (mixed well) and water or excipient with water were placed in a 70° C. oven for 6 hours. The weight of each component in the vials examined is detailed in Table 9.

TABLE 9

| Sample | Compound I (mg) | SLS (mg) | Poloxamer (mg) | Water (mg) | Total (mg) |
|---|---|---|---|---|---|
| C1 | 95.5 | | | 117.0 | 212.5 |
| C2 | 91.3 | 90.6 | | 219.3 | 401.2 |
| C3 | 92.1 | | 91.6 | 205.3 | 389.0 |
| C4 | | 94.0 | | 152.5 | 246.5 |
| C5 | | | 91.3 | 107.2 | 198.5 |

After 6 hours at about 70° C., the vials were removed and a visual observation recorded. The visual observation for each sample is summarized below in Table 10.

TABLE 10

| Sample | Visual observation |
|---|---|
| C1 | White powder suspension |
| C2 | White suspension |
| C3 | White suspension |
| C4 | Clear liquid (gel like) |
| C5 | Clear liquid (gel like) |

Based on the observations from Experiments A, B, and C, the wetting agent, poloxamer, was chosen for further exploration of color stability. Formulations containing either poloxamer or a different wetting agent, sodium laurel sulfate, were explored as detailed in Example 2 below.

Example 2

Study to Evaluate the Color Stability of Formulations Containing Compound I with Poloxamer or Sodium Laurel Sulfate Capsules of various formulations containing Compound I with either poloxamer or SLS (as exemplified by Formulation A and B detailed in Table 3) were manufactured and assessed for color stability under inlet air temperatures of 50° C., 60° C., or 70° C., in brief samples were taken during the manufacture of capsules using formulations containing Compound I and either 3% poloxamer, 8% poloxamer or 1.5% SLS. The samples were placed in amber glass bottles at various time points (2 min=initial sample after blending in fluid bed; 20 min=sample taken after granulation solution completely added; 30 min=Loss on Drying (LOD)≦4%; 100, 150 and 220 min=samples taken after LOD≦4% reached and continued to dry). Each sample was hand screened through a 30 mesh screen, the screened sample was placed in a separate white plastic weigh dish and visually assessed for color description. The results of this experiment are summarized in Table 11 below.

TABLE 11

| Formulation | Wetting Agent | Inlet Air Temp | 2 min | 20 min | 30 min | 100 min | 150 min | 220 min |
|---|---|---|---|---|---|---|---|---|
| A | 8% Poloxamer | 60° C. | + | + | + | +++ | ++++ | ++++ |
| A | 8% Poloxamer | 50° C. | + | + | + | ++ | +++ | +++ |
| B | 1.5% SLS | 70° C. | + | + | + | + | + | N/A |
| A | 3% Poloxamer | 70° C. | N/A | + | N/A | ++++ | N/A | N/A |

Scale
0 = white
+ = slight off white
++ = off white
+++ = slight yellow
++++ = yellow Capsules of Compound I containing SLS were found to have greater color stability than those containing poloxamer. In particular, the SLS formulation turned slight off white after the initial 2 min. blend and then remained color stable at later time points at an inlet air temperature of 70° C. In contrast, the poloxamer formulations turned slight yellow to yellow during the latter drying time points (100, 150, 220 min) at all inlet air temperatures.

Example 3

Study to Demonstrate the Dissolution Profiles of Formulations 1, 2, and 3

Aliquots of the granules for 10 mg capsules of Formulations 1, 2, and 3 detailed in Table 1, 2, and 4, respectively, were placed into capsules (without additional capsule fill) and their dissolution profile determined in accordance with the processes detailed below.

Formulations 1 and 2

The dissolution testing apparatus employed was a USPII apparatus Paddle Stirrer filled with 900 mL of dissolution medium consisting of 0.2% SLS solution buffered with pH 7.4 sodium phosphate buffer. The dissolution tests were conducted at 37° C.±0.5° C. The tests were carried out by stabilizing the dissolution medium at the test temperature with the paddle speed set at 75 RPM. Capsules were dropped into the dissolution medium with the paddles actuated. Periodically aliquot samples of the dissolution media were withdrawn and analyzed for Compound I content by UV spectroscopy at 293 nm for 1 capsules and by both UV spectroscopy at 293 nm and HPLC at 293 nm for 2 capsules (i.e., at the following post-drop timepoints for analysis by UV spectroscopy: 15, 30, 45, and 60 min; and at the following post-drop timepoints for analysis by HPLC: 5, 15, 30, 45, and 60 min). The total amount of Compound I present in the dissolution media was calculated based on the UV and/or HPLC determination at 293 nm and reported as a percentage of the total amount of Compound I initially contained in the capsule dissolved into the dissolution media. The dissolution data for a representative sample of capsules prepared according to Formulation 1 or Formulation 2 are shown in Table 12 below. Specifically, 12 capsules of Formulation 1 and 12 capsules of Formulation 2 were analyzed by UV spectroscopy at 293 nm, while 6 capsules of Formulation 2 were analyzed by HPLC at 293 nm. Likewise, the dissolution profile for Formulation 1 and 2 capsules are illustrated graphically in FIG. 1.

Formulation 3

The dissolution testing apparatus employed was a USPII apparatus Paddle Stirrer filled with 900 mL of dissolution medium consisting of 0.5% SLS solution buffered with pH 6.8 sodium phosphate buffer. The dissolution tests were conducted at 37° C.±0.5° C. The tests were carried out by stabilizing the dissolution medium at the test temperature with the paddle speed set at 75 RPM. Capsules were dropped into the dissolution medium with the paddles actuated. Periodically aliquot samples of the dissolution media were withdrawn and analyzed by HPLC at 293 nm for Compound I content (i.e., at the following post-drop timepoints: 5, 15, 30, 45, and 60 min). The total amount of Compound I present in the dissolution media was calculated based on the HPLC determination and reported as a percentage of the total amount of Compound I initially contained in the capsule dissolved into the dissolution media. The dissolution data for a representative sample of 12 Formulation 3 capsules are shown in Table 12 below. Likewise, the dissolution profile for Formulation 3 capsules is illustrated graphically in FIG. 1.

TABLE 12

| Formulation 1 UV Analysis Post-Drop Time (min) | Average % Compound I Dissolved of Samples | % Compound I Dissolved of Individual Samples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| 5 | — | — | — | — | — | — | — | — | — | — | — | — | — |
| 15 | 84 | 83 | 83 | 82 | 84 | 80 | 80 | 86 | 89 | 89 | 86 | 82 | 83 |
| 30 | 95 | 94 | 93 | 94 | 96 | 92 | 92 | 100 | 99 | 101 | 98 | 93 | 93 |
| 45 | 98 | 93 | 93 | 93 | 96 | 92 | 93 | 105 | 106 | 105 | 102 | 96 | 97 |
| 60 | 95 | 92 | 92 | 92 | 95 | 91 | 91 | 98 | 99 | 100 | 99 | 92 | 94 |

TABLE 12-continued

| Formulation 2 UV Analysis Post-Drop Time (min) | Average % Compound I Dissolved of Samples | % Compound I Dissolved of Individual Samples ||||||||||||
|---|---|---|---|---|---|---|---|---|---|---|---|---|---|
| | | 1 | 2 | 3 | 4 | 5 | 6 | 7 | 8 | 9 | 10 | 11 | 12 |
| 5 | — | — | — | — | — | — | — | — | — | — | — | — | — |
| 15 | 92 | 92 | 92 | 92 | 92 | 91 | 92 | 93 | 94 | 94 | 92 | 92 | 90 |
| 30 | 96 | 95 | 95 | 95 | 95 | 94 | 96 | 97 | 98 | 98 | 96 | 96 | 94 |
| 45 | 96 | 95 | 96 | 95 | 94 | 94 | 96 | 98 | 98 | 98 | 97 | 95 | 94 |
| 60 | 95 | 95 | 95 | 94 | 94 | 93 | 95 | 97 | 97 | 97 | 96 | 94 | 93 |

| Formulation 2 HPLC Analysis Post-Drop Time (min) | Average % Compound I Dissolved of Samples | % Compound I Dissolved of Individual Samples ||||||
|---|---|---|---|---|---|---|---|
| | | 1 | 2 | 3 | 4 | 5 | 6 |
| 5 | 79 | 74 | 76 | 86 | 71 | 90 | 77 |
| 15 | 95 | 96 | 95 | 95 | 93 | 95 | 94 |
| 30 | 95 | 96 | 95 | 95 | 95 | 95 | 95 |
| 45 | 94 | 95 | 93 | 95 | 94 | 95 | 94 |
| 60 | 93 | 94 | 94 | 93 | 94 | 93 | 94 |

| Formulation 3 HPLC Analysis Post-Drop Time (min) | Average % Compound I Dissolved of Samples | % Compound I Dissolved of Individual Samples ||||||||||||
|---|---|---|---|---|---|---|---|---|---|---|---|---|---|
| | | 1 | 2 | 3 | 4 | 5 | 6 | 7 | 8 | 9 | 10 | 11 | 12 |
| 5 | 83 | 84 | 87 | 43 | 87 | 85 | 87 | 86 | 84 | 87 | 88 | 87 | 85 |
| 15 | 99 | 98 | 99 | 99 | 98 | 97 | 101 | 98 | 98 | 100 | 101 | 99 | 97 |
| 30 | 100 | 100 | 100 | 101 | 100 | 98 | 102 | 99 | 99 | 101 | 101 | 100 | 99 |
| 45 | 100 | 100 | 100 | 100 | 99 | 98 | 102 | 99 | 98 | 101 | 101 | 99 | 99 |
| 60 | 99 | 99 | 99 | 99 | 98 | 97 | 101 | 98 | 98 | 100 | 100 | 98 | 99 |

The dissolution profiles of Formulations 1, 2, and 3 are suitable for immediate release. Of the three formulations examined, Formulation 3 dissolved more rapidly than either Formulation 1 or Formulation 2.

Example 4

Figure 2A:
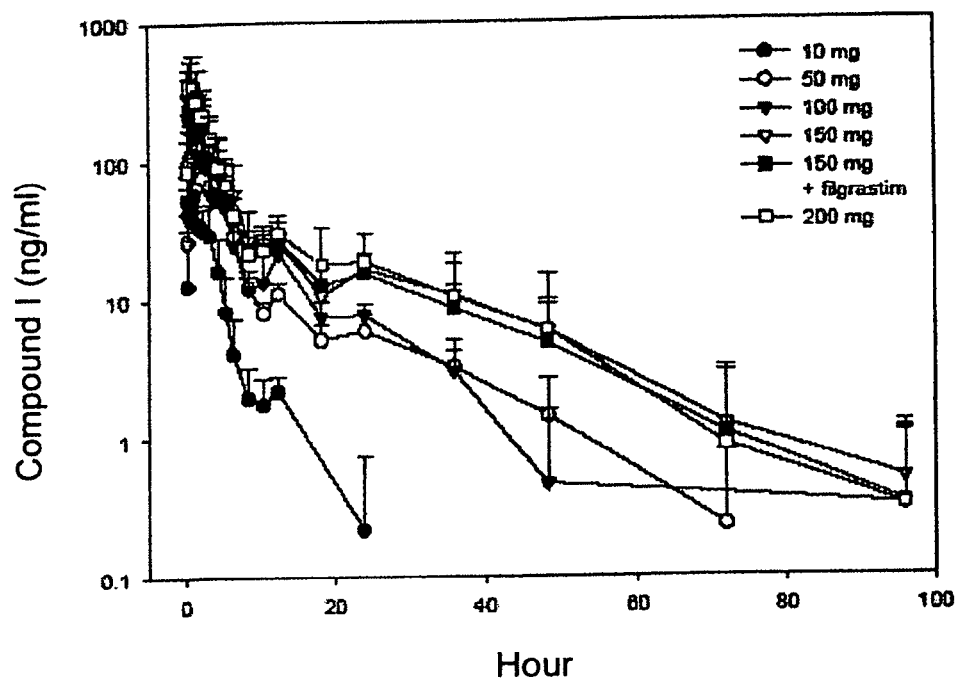
FIG. 2A depicts a log-linear plot and FIG. 2B depicts a linear-linear plot. Notably, error bars represent ±1 standard deviation. See Example 4, infra, for details.
Figure 2B:
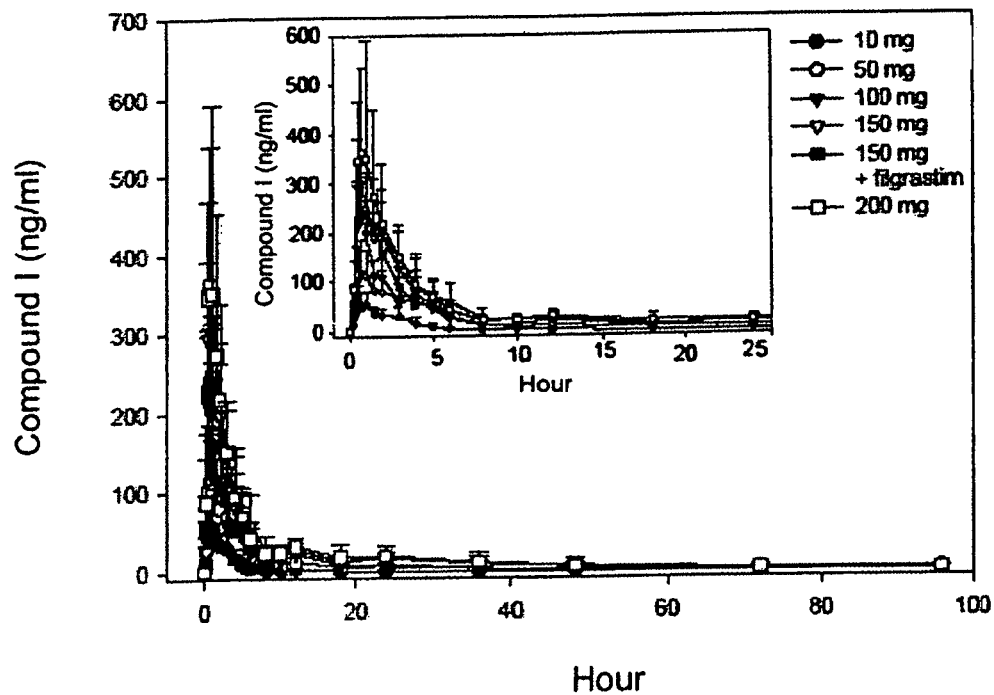

Clinical Studies to Demonstrate the Safety, Tolerability, and Pharmacokinetics of Compound I The safety, tolerability, and pharmacokinetics of Compound I using capsules of Formulation 1 were examined in healthy adult male and female human subjects in the following clinical studies:
  (i) single-dose oral administration of 10, 50, 100, 150 (in combination with or without 300 μg filgrastim (human G-CSF)), or 200 mg Compound I
  (ii) single-dose oral administration of 30 mg Compound I to fasted or fed subjects
  (iii) multiple-dose oral administration of 10, 30, or 50 mg Compound I The mean plasma concentration following single-dose oral administration of 10, 50, 100, 150 (with or without 300 μg filgrastim), or 200 mg Compound I is presented in FIG. 2A (log-linear plot) and FIG. 2B (linear-linear plot), Of note, the administration of 150 mg Compound I followed by administration of 300 Wig filgrastim did not alter the pharmacokinetic profile of Compound I. In addition, similar pharmacokinetic profiles were observed in the food-effect and multiple-dose studies (data not shown). That is, multiple peaks in the plasma concentration-time profiles were observed within 4 hours post dose in some subjects and there was a slight but consistent peak at 12 hours and 24 hours post dose.

Likewise, the mean pharmacokinetic parameters following single-dose oral administration of 10, 50, 100, 150 (with or without 300 μg filgrastim), or 200 mg Compound I is summarized in Table 13 below. In addition, the mean pharmacokinetic parameters following single-dose oral administration of 30 mg Compound I to healthy subjects under fed and fasted conditions is also summarized in Table 13 below

TABLE 13

| Dose Compound I (mg) | Cmax (ng/mL) Mean | CV (%) | Tmax (hr) Median | Range | Tf (hr) Mean | CV (%) |
|---|---|---|---|---|---|---|
| 10 | 73.8 | 35 | 1 | 0.5-3 | 14 | 35 |
| 50 | 153 | 27 | 0.75 | 0.5-4 | 46 | 35 |
| 100 | 261 | 34 | 0.75 | 0.5-4 | 38 | 13 |
| 150 | 364 | 19 | 0.75 | 0.5-2 | 64 | 39 |
| 150 (+Filgrastim) | 292 | 29 | 0.75 | 0.5-2 | 58 | 38 |
| 200 | 416 | 50 | 0.625 | 0.5-1 | 52 | 43 |
| 30 (fasted) | 147 | 7 | 0.75 | 0.5-4 | 40 | 27 |
| 30 (fed) | 122 | 46 | 2 | 0.5-6 | 32.3 | 29 |

| Dose Compound I (mg) | AUC (tf) (ng·hr/mL) Mean | CV (%) | AUC(I) (ng·hr/mL) Mean | CV (%) | $t^{1/2}$ (hr) Mean | CV (%) |
|---|---|---|---|---|---|---|
| 10 | 162 | 12 | NA[a] | NC | NA[a] | NC |
| 50 | 665 | 19 | 768[b] | 16 | 15.8[b] | 31 |
| 100 | 827 | 23 | 878 | 24 | 11.8 | 29 |

TABLE 13-continued

| 150 | 1534 | 23 | 1641 | 21 | 16.7 | 43 |
| 150 (+Filgrastim) | 1325 | 31 | 1378 | 29 | 13 | 37 |
| 200 | 1731 | 55 | 1808 | 53 | 11.3 | 33 |
| 30 (fasted) | 484 | 28 | 563[c] | 23 | 20.8[c] | 40 |
| 30 (fed) | 489 | 25 | 572[d] | 23 | 22.9[d] | 49 |

NA = not available; NC = could not be calculated (n < 3).
[a]Terminal elimination phase could not be determined in all subjects in this group.
[b]n = 4.
[c]n = 10.
[d]n = 7.

The relative bioavailability of Compound I following single-dose oral administration of 30 mg Compound I to healthy subjects under fed and fasted conditions is summarized in Table 14 below.

TABLE 14

| Compound I (mg) | Mean Cmax (ng/ml) | Mean AUC(tf) (ng · hr/ml) | Ratio Estimate[a] (%) | 90% Confidence Interval |
|---|---|---|---|---|
| 30 (fasted) | 147 | 484 | 82.9 | 60-115 |
| 30 (fed) | 122 | 489 | 102 | 92-113 |

[a]Percent ratio of the log-transformed mean values of treatment under fed relative to fasted conditions.

As reflected in the data above, there was no clinically meaningful effect of food on Cmax or AUC (tf) values of Compound I. The confidence interval for subjects receiving Compound I under fed relative to fasted conditions met the 80% to 125% bioequivalence criteria for AUC(tf), but not for Cmax. The mean Cmax value for subjects receiving Compound I with food was 17% lower than that of subjects receiving Compound I alone. However, this difference was not clinically meaningful.

The mean pharmacokinetic parameters following multiple-dose oral administration of 10, 30, or 50 mg Compound I to healthy subjects is summarized in Table 15 below.

the secondary absorption peaks and the limits of quantitation of the bioanalytical assay. The mean effective half-lives, based on accumulation ratios ranged from 6.94 to 11.0 hours and may be more reflective of the disposition of Compound I. The mean apparent total body clearance (CL/F) values ranged from 55.9 to 138 L/hr. The mean apparent volume of distribution (Vd/F) values ranged from 1469 to 2205 L.

Cmax and AUC increased in a dose-related, but not dose-proportional manner from 10 to 200 mg. The variability in the systemic exposure was low to moderate; coefficients of variation ranged from 19% to 50% and from 12% to 55% for Cmax and AUC, respectively.

Following multiple doses of Compound I, steady state was achieved by Day 11; Compound I Cmin values were similar on Days 11 through 14. There was little to no accumulation of Compound I observed in plasma on Day 14; mean accumulation ratio (R) values ranged from 1.05 to 1.21 (see, Table 15).

Example 5

Clinical Study to Demonstrate the Relative Bioavailability of Formulation 2 and Formulation 3

Figure 3:
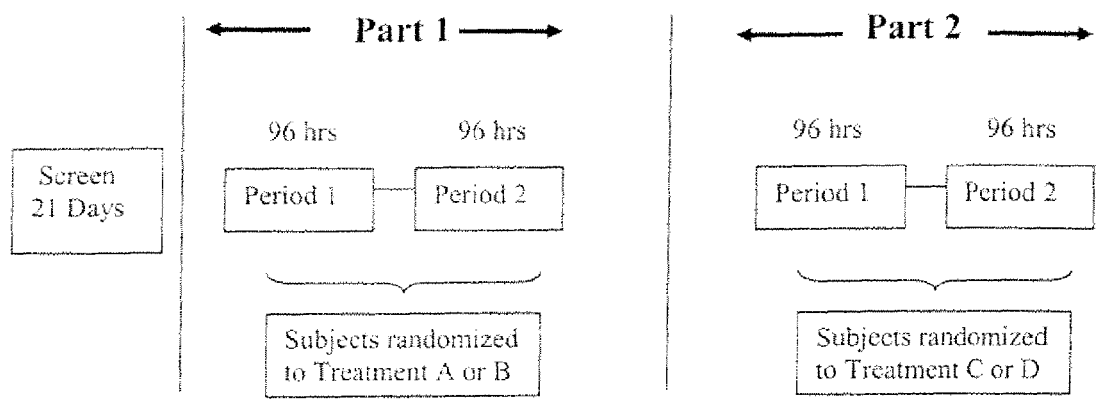
FIG. 3 illustrates a schematic of the clinical study designed to demonstrate the relative bioavailability of Formulation 2 and Formulation 3 based on a two-part, randomized, open-label, crossover study in healthy subjects.

This clinical study was designed to demonstrate the relative bioavailability of Formulation 2 and Formulation 3. This study, illustrated schematically in FIG. 3, is a two-part, randomized, open-label, crossover study in healthy male and female subjects.

Part 1 includes two periods with 16 subjects total crossed over to Treatments A and B as detailed below.

Treatment A: Single dose of Formulation 3, 10 mg capsule (fine granules).

Treatment B: Single dose of Formulation 2, 10 mg capsule

Each treatment was administered as a single dose on 4 separate occasions with a 96-hr washout period between each dose administered. Thus, each treatment period had a duration of 4 days. Each subject received Treatment A or Treat-

TABLE 15

| Dose Compound I (mg) | Day | Cmax (ng/mL) Mean | CV (%) | Tmax (hr) Median | Range | AUC (0-24 hr) (ng · hr/ml) Mean | CV (%) |
|---|---|---|---|---|---|---|---|
| 10 | 1 | 76 | 47 | 0.5 | 0.5-2 | 137 | 25 |
| 30 | | 173 | 31 | 0.5 | 0.5-1.5 | 397 | 24 |
| 50 | | 239 | 24 | 0.75 | 0.5-2 | 681 | 20 |
| 10 | 14 | 78.1 | 42 | 0.5 | 0.5-1 | 156 | 28 |
| 30 | | 159 | 24 | 0.5 | 0.5-0.75 | 414 | 26 |
| 50 | | 279 | 30 | 0.5 | 0.5-0.75 | 825 | 28 |

| Dose Compound I (mg) | Day | $t^{1/2}$ (hr) Mean | CV (%) | R Mean | CV (%) |
|---|---|---|---|---|---|
| 10 | 1 | NC | NC | NA | NA |
| 30 | | NC | NC | NA | NA |
| 50 | | NC | NC | NA | NA |
| 10 | 14 | NC | NC | 1.14 | 9 |
| 30 | | NC | NC | 1.05 | 13 |
| 50 | | 13.8[a] | 46 | 1.21 | 17 |

NA = not available; NC = could not be calculated (n < 3).
[a]n = 7.

As reflected in the data from these studies, Compound I was rapidly absorbed. Median max values ranged from 0.5 to 2 hours post dose. The mean terminal elimination t½ ranged from 11.3 to 22.9 hours. The terminal elimination phase of some subjects could not be determined mainly as a result of ment B in the AM of Day 1. That is, one 10 mg capsule of Formulation 3 (Treatment A) or Formulation 2 (Treatment B), administered as a single oral dose with 240 ml of water. Serial blood samples for Compound I pharmacokinetic evaluation were collected pre-dose (0 hour), as well as 0.5, 1, 2, 4, 6, 8, 12, 24, 48, 721 and 96 hours post-dose. Of note, the 96-hour sample from Part 1 Period 1 serves as the pre-dose sample for Part 1 Period 2.

The plasma concentration of Compound I for each blood sample collected is determined. An exemplary assay to determine the plasma concentration of Compound I follows. In brief, calibration standards, QC samples, study samples and zero standards (blanks with IS) are prepared by pipetting 500 µL of the respective plasma sample and 25 µL of the IS working solution (0.100 µg/mL).

Control blanks (plasma without IS) are prepared by pipetting 525 µL of control plasma into a dilution tube. All samples are diluted with 200 µL of a 10 mM ammonium acetate with 0.1% acetic acid solution.

Pre-wash extraction cartridge (Water Oasis, 1 m) with 1.0 mL of methanol and centrifuge for 3 min at 3000 rpm, followed by addition of 1.0 mL of 10 mM ammonium acetate with 0.1% acetic acid. Centrifuge again for 3 minutes at 3000 rpm. Wash with 1.0 mL of 10 mM ammonium acetate with 0.1% acetic acid. Centrifuge for 5 min at 2000 rpm. Wash each cartridge with 1.0 mL of deionized water and centrifuge for 5 min at 2000 rpm. Elute compound with from the cartridge with 1.0 mL aliquots of methanol. Evaporate eluent to dryness at 40° C. under gentle stream of air. Reconstitute the residue with 0.3 mL of 50:50, v:v % methanol:water solution into a 96 well assay plate. A 10 to 40-µL aliquot is injected into the LC-MS/MS system for analysis. A 5 to 10-µL aliquot is injected into the LC-MS/MS system for analysis.

The HPLC system employs a 4.6×50 mm (5 µm particle size) Luna Phenyl-Hexyl column with a flow rate of 1.0 mL/min of Mobile Phase A (0.1% formic acid in water) and Mobile Phase 8 (0.1% formic acid in acetonitrile) in a gradient step program to separate the analyte and IS from the bulk of the matrix components. The retention times of SCH 527123, and the IS are approximately 1.2 min. The analyte and IS are detected using an API 4000 triple quadrupole LC-MS/MS System equipped with a TurbolonSpray ionization source.

Using non-compartmental analysis, the plasma concentration of Compound I is used to derive the following pharmacokinetic parameters: Cmax, Tmax, and AUC(tf) to determine the relative bioavailability of Formulation 2 with Formulation 3.

Part 2 includes two periods with 16 subjects total crossed over to Treatments C or D as detailed below.
Treatment C: Single dose of Formulation 3, 10 mg capsule (fine granules).
Treatment D: Single dose of Formulating 3, 10 mg capsule (coarse granules).

Even though Part 1, Treatment A and Part 2, Treatment C utilize the same Formulation, the subjects participating in Part 2 are not the same as those who participated in Part 1.

Each treatment is administered as a single-dose on 4 separate occasions with a 96-hr washout period between each dose administered. Thus, each treatment period has a duration of 4 days. Each subject receives a single dose of Treatment C or Treatment D in the AM of Day 1. That is, one 10 mg capsule of Formulation 3 fine granules (Treatment C) or Formulation 3 coarse granules (Treatment D), administered as a single oral dose with 240 ml of water. Serial blood samples for Compound I pharmacokinetic evaluation are collected pre-dose (0 hour), and 0.5, 1, 2, 4, 6, 8, 12, 24, 48, 72, and 96 hours post-dose. The 96-hour sample from Part 2 Period 1 also serves as the pre-dose sample for Part 2 Period 2.

The plasma concentration of Compound I for each blood sample collected is determined. Using non-compartmental analysis, the plasma concentration of Compound I is used to derive the following pharmacokinetic parameters: Cmax, Tmax, and AUC(tf) to determine the relative bioavailability of Formulation 3 fine granules with Formulation 3 coarse granules.

The inventors believe that Formulation 2 provides comparable bioavailability to Formulation 3, In addition, the inventors believe that capsules containing fine granules of Formulation 3 provide at least comparable bioavailability to capsules containing coarse granules of Formulation 3.

Example 6

Clinical Study to Demonstrate the Effect of Compound I in Subjects with Moderate to Severe COPD This clinical study was designed to demonstrate the effect of Compound I using capsules of Formulation 2 or Formulation 3 in subjects with moderate to severe COPD. This study, illustrated schematically in FIG. 4, is a double-blind, placebo-controlled, randomized, two-part study in subjects with moderate to severe COPD.

Figure 4A:
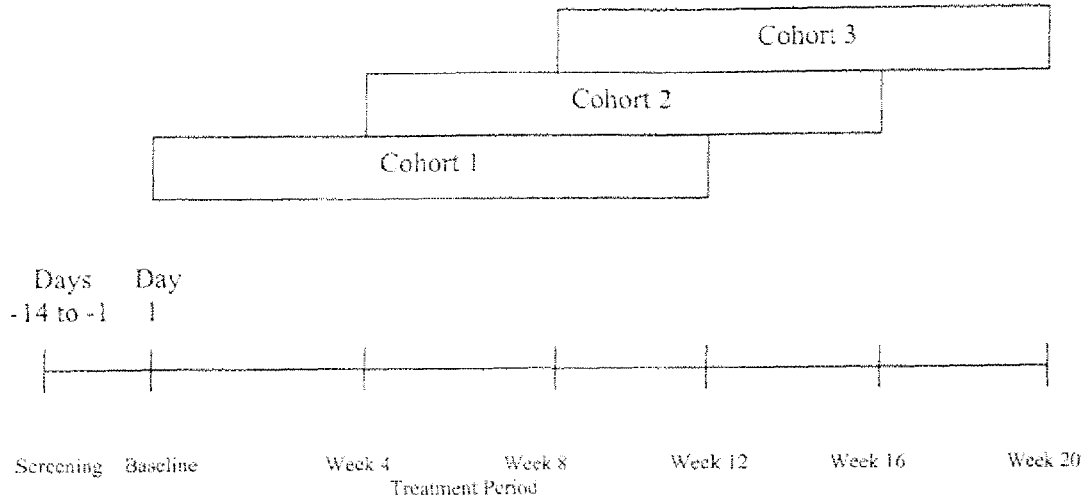
FIG. 4A and FIG. 4B depict Part 1 (involving Cohorts 1-3) and Part 2 (involving Cohort 4), respectively, of this clinical study.

Part 1 is a double-blind, placebo-controlled, randomized, rising-dose study consisting of four treatment groups enrolled in three cohorts (FIG. 4A). The treatment period for each cohort is 12 weeks in duration. The target sample size is 30 subjects per cohort with an Compound I to placebo ratio of 2:1 as illustrated in Table 15 below.

TABLE 15

| Cohort | Placebo | Compound I | | |
| | | 3 mg | 10 mg | 30 mg |
| --- | --- | --- | --- | --- |
| 1 | 10 | 20 | — | — |
| 2 | 10 | — | 20 | — |
| 3 | 10 | — | — | 20 |

The safety and tolerability of three dose levels (i.e., 3, 10, and 30 mg) of Compound I using capsules of Formulation 2 compared to placebo is based on adverse events, changes from Baseline for both absolute and percent sputum neutrophil counts, and peripheral blood neutrophil (PBN) counts. After completing the safety analyses for Part 1 for Cohorts 1-3, Part 2 is conducted as detailed below.

Figure 4B:
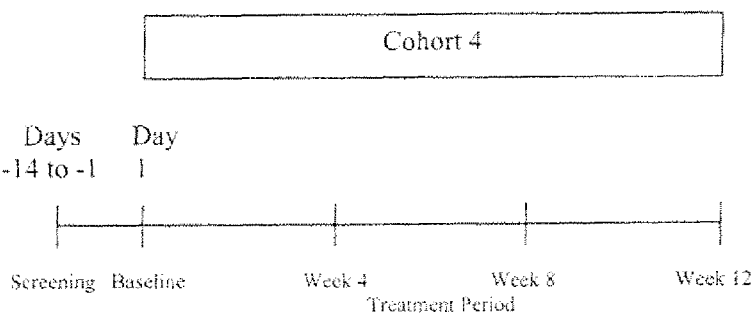

Part 2 is a double-blind, placebo-controlled, randomized, parallel group study consisting of four treatment groups enrolled as one cohort (FIG. 4B). The treatment period for Cohort 4 is 12 weeks in duration. The target sample size is 125 subjects per arm as illustrated in Table 16 below.

TABLE 16

| Cohort | Placebo | Compound I | | |
| | | 3 mg | 10 mg | 30 mg |
| --- | --- | --- | --- | --- |
| 4 | 125 | 125 | 125 | 125 |

As in Part 1, the safety and tolerability of three dose levels (i.e., 3, 10, and 30 mg) of Compound I using capsules of Formulation 3 compared to placebo is based on adverse events, changes from Baseline for both absolute and percent sputum neutrophil counts, as well as PBN counts. In addition, the effectiveness of these dose levels is based on the following criteria:
changes from Baseline in pre-bronchodilator forced expiratory volume in first second (FEV1) and changes from Baseline in the daily AM/PM of the sum of the individual symptoms of sputum production, cough, and dyspnea score (SCDS), both as longitudinal averages over the 12-week treatment period changes from Baseline at each visit or interval in post-bronchodilator FEV1, forced expiratory flow during the middle half of the forced vital capacity (FEF25%-75%), FVC, functional residual capacity (FRC), COPD exacerbations, individual symptom scores, SODS, and individual, as well as total, domains of Saint George's Respiratory Questionnaire (SGRQ).

Safety data are tabulated from the pooled study population, and include adverse events, laboratory results including PBN counts, and results of pulmonary function tests.

Efficacy analyses are based solely on data collected from Part 2, Cohort 4 wherein the primary efficacy parameters measured are changes from Baseline in FEV1 and changes from Baseline in SCDS, both examined as longitudinal averages over the 12-week treatment period. Estimates of treatment effects on changes from Baseline in all of the continuous efficacy parameters are derived from the primary analysis of variance (ANOVA) mixed-effects longitudinal model. The fixed-effects are treatment (four levels) and time. Random effects are the intercept and slope over time, for each subject. The primary analysis is based on two comparisons of the high dose vs. placebo (one for each efficacy parameter). The Hochberg method for multiplicity adjustment for the two coprimary parameters is applied to ensure that the overall error rate across parameters does not exceed 4.9%. To protect the overall error rate at 4.9% with respect to doses, a stepdown procedure is applied. Specifically, if the high dose is significantly better than placebo for only one of the two primary parameters under the Hochberg adjustment, the middle dose is compared to placebo for this same endpoint at alpha=4.9%, and then if significant, the low dose is compared to placebo for this same endpoint at alpha=4.9%. If, on the other hand, the high dose is significantly better than placebo for both primary endpoints, the middle dose is compared to placebo for both primary endpoints under the Hochberg adjustment. Finally, the stepdown procedure from the middle to the low dose is analogous to that described above for the high to the middle dose stepdown procedure.

Confidence intervals (Cis) are determined from the estimates derived from these models for the differences between each Compound I dose group and placebo. Assessments are made at each visit/weekly interval as well as at the endpoint (last observation carried forward) of treatment. The by-visit/interval analysis model extracts sources of variation due to treatment.

Proportions of subjects with exacerbations are assessed (analyzed by a Cochran-Mantel-Haenszel model), and if sufficient numbers of events are observed, time to first exacerbation (analyzed by logrank test which includes treatment in the model), and per-subject, per-year exacerbation rates (analyzed by Wilcoxon rank-sum test).

Note that all analyses are based on all randomized subjects with both Baseline and at least some post-Baseline data. Since subjects receive their first dose at the study center and diary data are collected daily, very few (if any) subjects are expected not to be included in the analyses; subjects with partial missing data are, specifically, included in these analyses. The choice of the primary model, a longitudinal analysis, ensures that such subjects with partial data can be analyzed. Supportive analyses are performed for the primary parameters to assess the potential impact of missing data.

The inventors believe that Compound I provides a reduction in sputum neutrophil and peripheral blood neutrophils, thereby improving symptoms, pulmonary function, quality of life, and sputum production in subjects with moderate to severe COPD. Compound I is thus useful for preventing or delaying the progression of COPD, and subsequent deterioration of pulmonary function.

Example 7

Figure 5A:
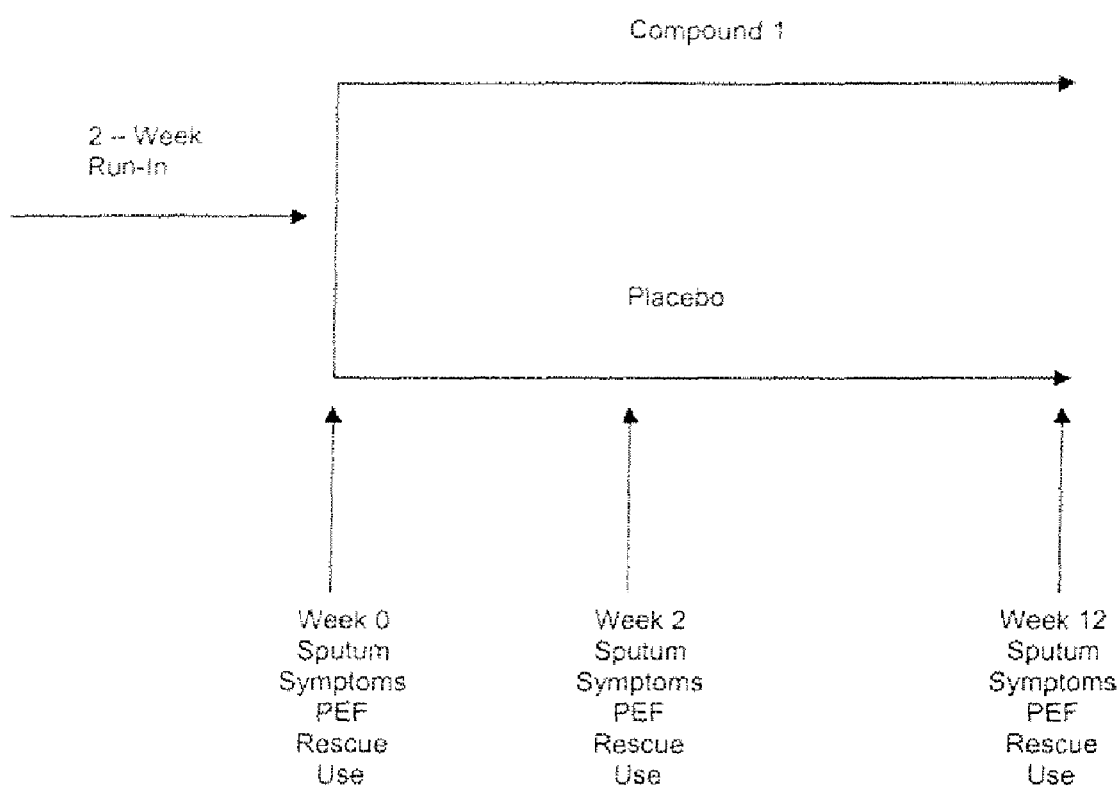
FIG. 5A depicts Steps 1 and 2 of this study.
Figure 5B:
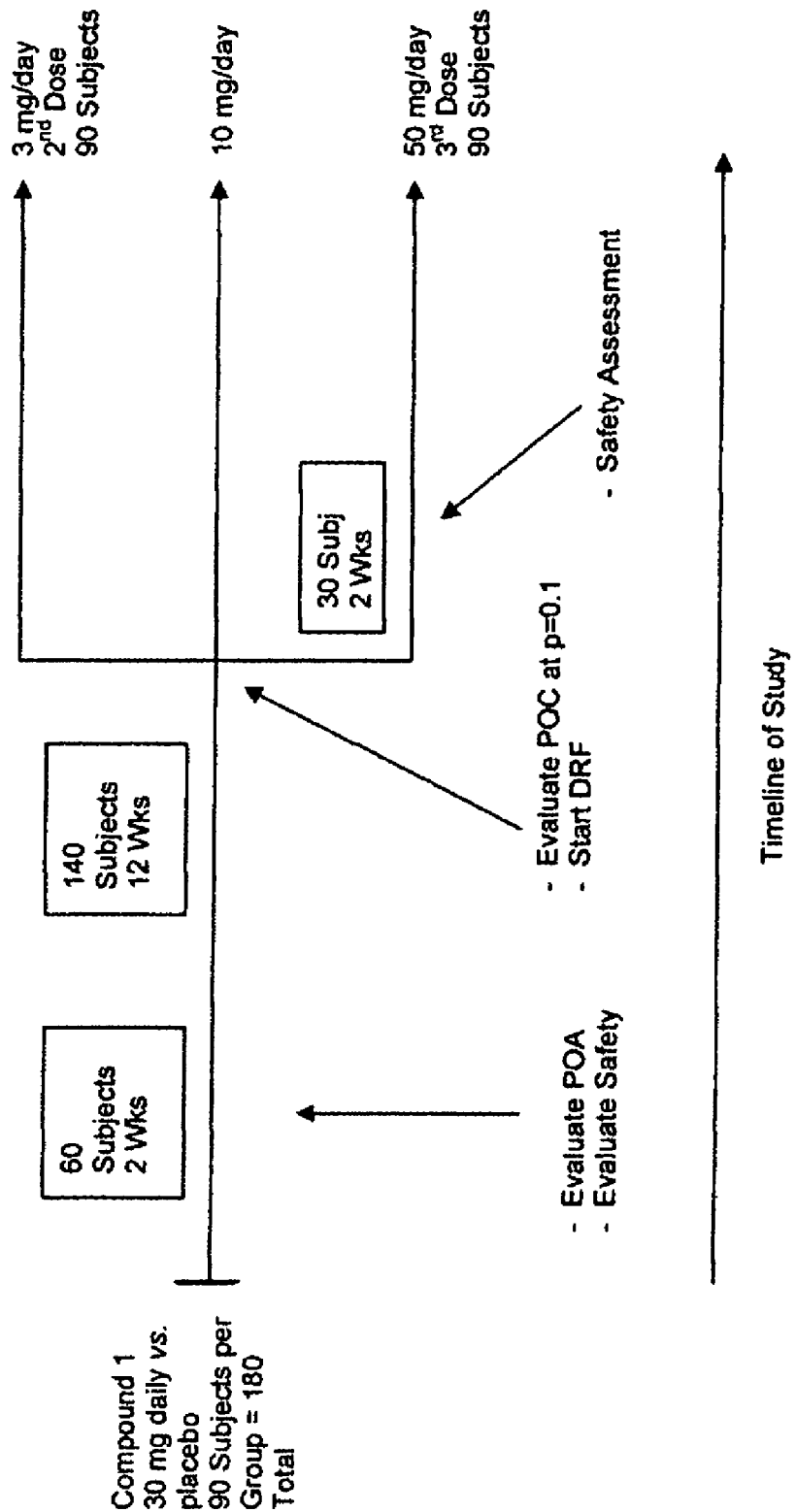
FIG. 5B depicts Steps 1-3 of this study.

Clinical Study to Demonstrate the Effect of Compound I in Subjects with Severe Neutrophilic Asthma This clinical study was designed to demonstrate the effect of Compound I using capsules of Formulation 3 in subjects with severe neutrophilic asthma. This study, illustrated schematically in FIG. 5, is a randomized, double-blind, placebo-controlled study in subjects with severe neutrophilic asthma.

This study follows an adaptive design to assess the following three objectives:

Step 1: Proof of Activity (POA), to demonstrate that Compound I can reduce sputum neutrophils in subjects with severe neutrophilic asthma.

Step 2: Proof of Concept (POC), to demonstrate that Compound I is effective in reducing the number of asthma exacerbations in subjects with severe asthma.

Step 3: Dose-Range Finder (DRF), to determine dose response based on the reduction in asthma exacerbations.

Step 1 and Step 2 of the study enrolls approximately 140 subjects who are treated with 30 mg Compound I or placebo for a total of 12 weeks. Once approximately 60 subjects have completed 2 weeks of treatment, the safety of the drug as well as POA of Compound I is evaluated. A clinically significant change in sputum neutrophils, i.e. reduction of 25% from Baseline through 2 weeks of treatment with Compound I compared to placebo, demonstrates POA (Step 1).

Once approximately 140 subjects have completed 12 weeks of treatment, safety and POC (efficacy) of Compound I is evaluated. A trend in the reduction of asthma exacerbations with Compound I compared to placebo demonstrates POC (Step 2).

The DRF segment of the study (Step 3) begins wherein subjects in the 30 mg Compound I and placebo treatment groups continue while two additional dose arms are introduced. Two out of the following three once daily (QD) doses: 3 mg, 10 mg, or 50 mg Compound 1, are selected as the two additional dose arms based on the evaluation of subjects in the 30 mg Compound I treatment group. Safety is assessed after approximately 30 subjects have completed 2 weeks of treatment in DRF. Variables include the effect on sputum neutrophils, PBNs, adverse events (AEs) and other safety data. Approximately 90 subjects are enrolled in each of the new treatment groups and 20 subjects in the 30 mg Compound I and placebo groups.

Primary Efficacy Endpoint: The primary efficacy endpoint is the asthma exacerbation status ('yes' for presence of an exacerbation, 'no' for absence) during the 12-week treatment period.

A mild asthma exacerbation is defined as fulfillment of at least one of the following criteria:

Two consecutive days, based on 24-hour diary data:
  Any night with awakenings due to asthma.
  Morning peak expiratory flow (PEF) 20% or more below Baseline (average of AM PEF during the 2-week Run-In Period).
  As-needed rescue medication involving the use of two inhalations or more (above Baseline) within 24-hours (Baseline value established as the average 24-hour as-needed rescue medication used during the Run-In Period).

A severe asthma exacerbation is defined as fulfillment of at least one of the following criteria:
- Any study visit with a 20% drop (from Baseline) in post-bronchodilator FEV1.
- An exacerbation requiring a hospital or emergency room visit.
- A change in medication requiring the use or increase of systemic steroids.

Secondary Efficacy Endpoints: Secondary efficacy endpoints are changes from Baseline in the daily AM/PM asthma symptoms, FEV1, PEF, overall quality-of-life (QOL), reduction in sputum neutrophils, and time to first exacerbation.

Statistical Methods: The statistical model, for the change from Baseline in sputum neutrophils, is a one-way analysis of variance (ANOVA) with treatment as the factor. Confidence intervals of 95% are based on the least square means from the ANOVA. The statistical analysis used for the primary efficacy variable of the asthma exacerbation status is based on the chisquare test. In addition, time to the first asthma exacerbation is analyzed using the logrank test. POA is tested at alpha=0.10, two-tailed, DRF is tested at alpha=0.05 two-tailed. A stepdown approach is used: comparison to placebo is made first for the highest dose of Compound 1, then if significant, for the middle dose, and finally, if both are significant, for the lowest dose.

The inventors believe that Compound I provides a reduction in asthma exacerbation thereby improving daily AM/PM asthma symptoms, FEV1, PEF, overall quality of life, and sputum production and time to first exacerbation in subjects with severe neutrophilic asthma. Compound I is thus useful for treating neutrophilic asthma.

Example 8

Figure 6A:
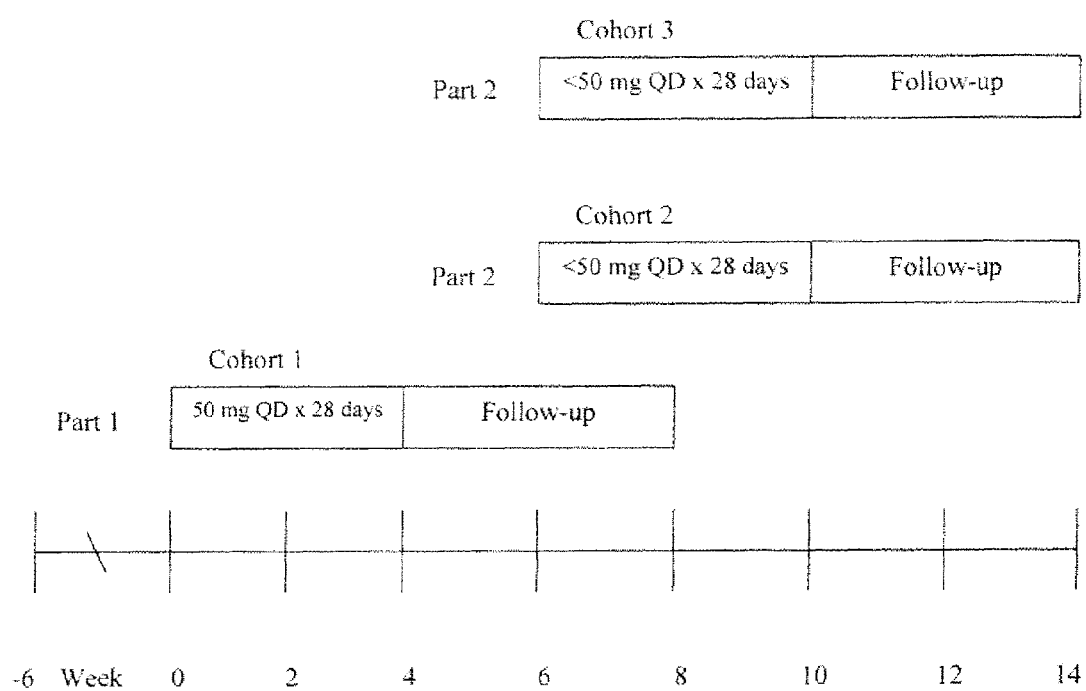
FIG. 6A depicts Parts 1 and 2.

Clinical Study to Demonstrate the Effect of Compound I in Subjects with Severe Psoriasis This clinical study was designed to demonstrate the effect of Compound I using capsules of Formulation 2 in subjects with severe psoriasis. This study, illustrated schematically in FIG. 6A, was designed as a prospective, randomized, double-blind, placebo-controlled, parallel-group study in subjects with moderate to severe psoriasis.

Figure 6B:
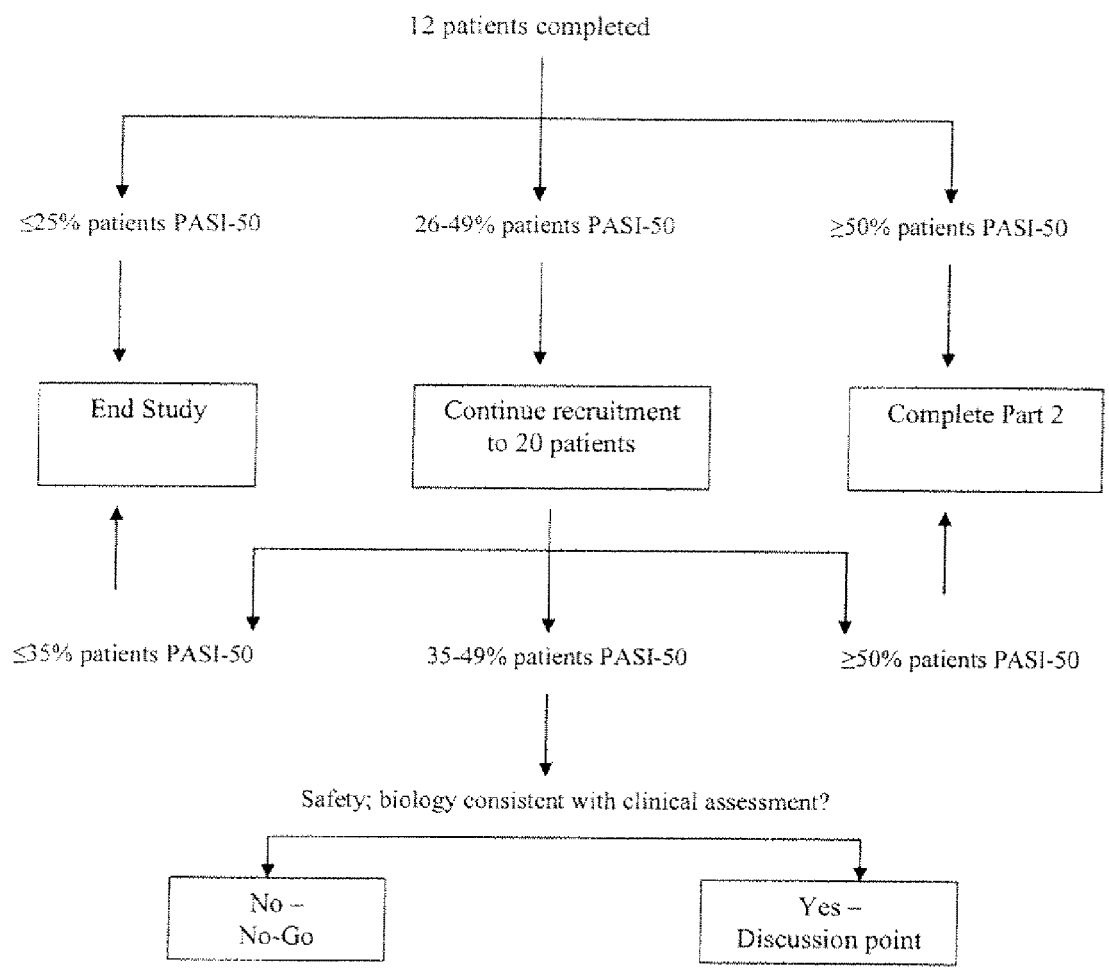
FIG. 6B depicts the progression of this study.

In Part 1, 21 subjects are randomized to either 50 mg Compound I once daily or matched placebo in a 2:1 ratio. Each treatment is administered for 28 days. After twelve patients have completed dosing, a determination is made on the progression of the study as outlined in FIG. 6B. At either interim or final analysis, if ≧50% of patients receiving Compound I have a 50% decrease in PASS, and no subjects in the placebo group have a 50% decrease in PASI, Part 2 of the study commences.

In Part 2, 15 subjects are randomized to one of two doses of Compound I each of which is less than 50 mg once daily or matched placebo in either a 2:2:1 ratio or 1:1:1 ratio. The dose levels of Compound I selected are based on the safety and activity results of Part 1.

Clinical Assessment. At Screening, Baseline, and Days 1, 8, 15, 29, 36, and 57 the clinical psoriasis activity (PASI and physician global assessment) is determined for each patient.

Pharmacodynamic Assessment: At Baseline and Day 29, the following evaluations are made for each of the treatment groups:

- immunohistochemistry of psoriatic plaque for the staining of CD66b CD50, Cathepsin G, and CD3+, CD4+, CD8+ leukocytes
- determination of mRNA expression of Gro-α, IL-8, and CXCR2 in the psoriatic plaque and peripheral blood
- plasma chemokine concentrations including Gro-α and IL-8
- blood microarray analysis Pharmacokinetic Assessment. Blood samples are obtained during each outpatient visit and the plasma concentration of Compound I determined. The trough concentration (Cmin) of Compound I is assessed to verify subject compliance.

An exemplary assay to determine the plasma concentration of Compound I follows. In brief, calibration standards, quality control samples, study samples and zero standards (blanks with investigational samples (IS)) are prepared by pipetting 200 μL of the respective plasma sample and 25 μL of the IS working solution (0.500 μg/mL IS in blank plasma) into a dilution tube. Control blanks (plasma without IS) are prepared by pipetting 225 μL of control plasma into a dilution tube. All samples are diluted with 200 μL of a 10 mM ammonium acetate with 0.1% acetic acid solution.

Following preparation, the samples are loaded onto a 96-well Varian Polaris C18 extraction plate that has been conditioned with 450 μL of methanol and then with 450 μL of 10 mM ammonium acetate with 0.1% acetic acid. The SPE plate is then washed with 450 μL of 10 mM ammonium acetate with 0.1% acetic acid, and 450 μL of methanol/water (5:95, v:v %). The analytes and IS are eluted from the SPE plate with two 100-μL aliquots of methanol/water (50:50, v:v %) into a 96 well assay plate. A 10 to 40-μL aliquot is injected into the LC-MS/MS system for analysis.

The HPLC system employed a 4.6×50 mm (5 μm particle size) Phenomenex Phenylhexyl column with a flow rate of 1.00 mL/min of Mobile Phase A (0.1% formic acid in water) and Mobile Phase B (0.1% formic acid in acetonitrile) in a gradient step program to separate the analyte and IS from the bulk of the matrix components. The retention times of Compound I, and the IS are approximately 1.6 min. The analyte and IS are detected using an API 4000 triple quadrupole LC-MS/MS System equipped with a TurbolonSpray ionization source.

Safety Assessment: Blood samples for clinical laboratory tests, vital signs and ECGs are obtained at specified times for safety evaluation. Subjects are observed and questioned on visit days for the possible occurrence of adverse events (AEs). Additionally, the subject records the occurrence of AEs during outpatient days on their diary cards.

Efficacy Analyses: The primary efficacy endpoint is the response defined as a ≧50% decrease from baseline in the PASI at the end of 28 days of treatment as well as PGA. The data for the secondary endpoints detailed below are listed and summarized by treatment group using descriptive statistics. Specifically,

- percent reduction on Day 28 relative to baseline of psoriatic plaque cellularity, with subpopulation analysis of neutrophils (CD50, Cathepsin G) and T-lymphocytes (CD3+, CD4+, CD8+)
- change from baseline in mRNA expression of Gro-α, IL-8, and CXCR2 in the psoriatic plaque and peripheral blood
- change from baseline in plasma chemokine concentrations including Gro-α and IL-8

Safety Analysis: Clinical safety laboratories, vitals, and ECGs are summarized using descriptive statistics. Adverse events are tabulated by treatment groups. ECGs are summarized descriptively by day and time for each treatment group. All other safety parameters are listed.

The inventors believe that Compound I provides a reduction in PASI in subjects with severe psoriasis. Compound I is thus useful for treating psoriasis.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A composition comprising Compound I or a pharmaceutically acceptable salt thereof and at least one pharmaceutically acceptable excipient which provides release of at least 83% Compound I in 5 minutes when tested using a USPII Paddle Stirrer apparatus filled with 900 mL of dissolution medium consisting of 0.5% sodium lauryl sulfate solution buffered with pH 6.8 sodium phosphate buffer at 37° C.±0.5° C. with the paddle speed set at 75 RPM, wherein Compound I has the chemical structure

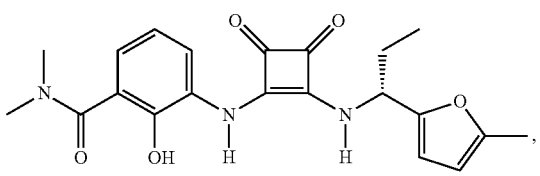

and wherein the at least one pharmaceutically acceptable excipient is
one or more wetting agent(s), which is sodium lauryl sulfate present in a range of 0.1% to 5% (w/w),
one or more binder(s), which is povidone present in a ratio of povidone to Compound I of between 0.18:1 to 1.8:1,
one or more diluent(s), and
one or more disintegrant(s), which is crospovidone present at about 2% to about 30% (w/w); and
wherein the composition is a capsule.

2. The composition of claim 1, which provides release of at least 99% Compound I in 15 minutes.

3. The composition of claim 1, wherein the composition is color stable as assessed by comparing the color of a first sample taken after blending Compound I, one or more wetting agent(s), one or more binder(s), one or more diluent(s), and one or more disintegrant(s) in a fluid bed with a second sample taken after loss on drying 4% reached under an inlet air temperature of 70° C. and the second sample is continued to dry under the inlet air temperature of 70° C. for at least 80 minutes.

4. The composition of claim 1, wherein one or more wetting agent(s) is sodium lauryl sulfate present in a ratio of sodium lauryl sulfate to Compound I of about 1 to 10.

5. The composition of claim 1, wherein one or more wetting agent(s) is sodium lauryl sulfate present in a range of about 0.1% to about 2% (w/w).

6. The composition of claim 1, wherein one or more binder(s) is povidone present at about 0.1% to about 20% (w/w).

7. The composition of claim 1, wherein one or more binder(s) is povidone present in a ratio of povidone to Compound I of between about 0.66 to 1.

8. The composition of claim 1, wherein one or more binder(s) is povidone present at about 0.3% to about 5% (w/w).

9. The composition of claim 1 wherein one or more diluent(s) is present at about 10% to about 90% (w/w).

10. The composition of claim 9, wherein one or more diluent(s) is microcrystalline cellulose and lactose.

11. The composition of claim 1, further comprising one or more glidant(s).

12. The composition of claim 11, wherein one or more glidant(s) is present at about 0.1% to about 5% (w/w).

13. The composition of claim 11, wherein one or more glidant(s) is silicon dioxide.

14. The composition of claim 1, further comprising one or more lubricant(s).

15. The composition of claim 14, wherein one or more lubricant(s) is present at about 0.2% to about 5% (w/w).

16. A composition comprising the following components:

| Components | mg per unit dose of composition |
|---|---|
| Compound I | 10 |
| Lactose Monohydrate | 108.02 |
| Microcrystalline Cellulose | 35.2 |
| Crospovidone | 16.5 |
| Povidone | 5.28 |
| Sodium Lauryl Sulfate | 1 | wherein Compound I has the chemical structure

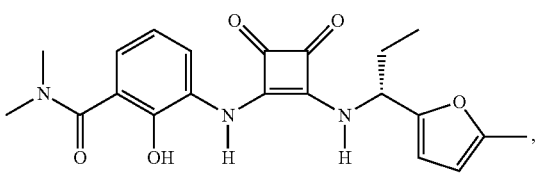

and
wherein the composition is a capsule.

17. The composition of claim 16, further comprising the following components:

| Components | mg per unit dose of composition |
|---|---|
| Microcrystalline Cellulose | 24.2 |
| Crospovidone | 16.5. |

18. The composition of claim 16, further comprising the following components:

| Components | mg per unit dose of composition |
|---|---|
| Silicon Dioxide | 2.2 |
| Magnesium Stearate | 1.1. |

19. The composition of claim 1, which exhibits a mean AUC of Compound I between about 484 ng.hr/ml and about 489 ng.hr/ml following a single-dose oral administration of 30 mg Compound I to a human.

20. The composition of claim 1, which exhibits a mean Cmax of Compound I between about 122 ng/ml and about 147 ng/ml following a single-dose oral administration of 30 mg Compound I to a human.

21. The composition of claim 1, which exhibits a median Tmax of Compound I between about 0.5 and about 2 hours following oral administration to a human.

22. A method for treating an inflammatory disorder in a patient suffering therefrom comprising administering the composition of claim 1, wherein the inflammatory disorder is selected from acute inflammatory pain, arthritis, chronic obstructive pulmonary disease (COPD), psoriasis, and asthma.

23. The composition of claim 1, wherein one or more binder(s) is povidone present at about 2% to about 3% (w/w).

24. The method of claim 22, wherein the inflammatory disorder is chronic obstructive pulmonary disease (COPD).

* * * * *